United States Patent [19]

Srour et al.

[11] Patent Number: 5,672,346
[45] Date of Patent: Sep. 30, 1997

[54] HUMAN STEM CELL COMPOSITIONS AND METHODS

[75] Inventors: Edward Srour, Indianapolis, Ind.; Esmail Zanjani, Reno, Nev.; John E. Brandt; Ronald Hoffman, both of Indianapolis, Ind.

[73] Assignee: Indiana University Foundation, Bloomington, Ind.

[21] Appl. No.: 77,134

[22] Filed: Jun. 15, 1993

Related U.S. Application Data

[63] Continuation-in-part of Ser. No. 919,447, Jul. 27, 1992, abandoned.

[51] Int. Cl.[6] .................................................. A61K 35/14
[52] U.S. Cl. ................................................. 424/93.7
[58] Field of Search ....................... 435/2, 240.1, 240.21, 435/240.25; 424/93 U, 93 V, 93.7, 520

[56] References Cited

PUBLICATIONS

Sustained human hematopoiesis in sheep transplanted in utero during early gestation with fractionated adult human bone marrow cells. Srour et al. Blood Mar 15 1992, 79 (6) pp. 1404–1412.
Linch et al. (1986) The Lancet Dec. 20/27: p. 1453.
Palavicini et al. (1991) Clinical Research 39(2):378A.
Fleishman and Mintz (1979) P.N.A.S. 76(11):5736–5740.
Fleishman and Mintz (1984) J. Exp. Med. 159:731–745.
Diukman and Golbus (1992) Journal of Reproductive Medicine 37(6):515–520.
Slavin et al. (1992) Bone Marrow Transplant. 1:189–190.
Touraine et al.; Transplantation Proceedings, vol. 21, No. 1; pp. 3112–3113; Feb. 1989.
Srour et al.; Cytometry, vol. 12, pp. 179–183; 1991.
Srour et al.; Blood Cells, vol. 17, pp. 287–295; 1991.
Briddell et al.; Blood, vol. 79, No. 12, pp. 3159–3167; Jun. 15, 1992.
Brandt et al.; Blood, vol. 79, No. 3, pp. 634–641 Feb. 1, 1992.
Flake et al.; Science, vol. 233, pp. 776–778; Aug. 15, 1986.
Bernstein et al.; Blood, vol. 77, pp. 2316–2321; Jun. 1, 1991.
Papayannopoulou, et al.; Blood, vol. 78, pp. 1403–1412; Sep. 15, 1991.

*Primary Examiner*—George C. Elliott
*Attorney, Agent, or Firm*—Bertram I. Rowland; Pamela J. Sherwood

[57] ABSTRACT

Disclosed are human pluripotent hematopoietic stem cell (PHSC) enriched compositions and methods for obtaining and using the compositions. A substantially homogeneous population of human hematopoietic cells characterized as $CD34^+$, $HLA-DR^-$, and c-kit receptor positive ($KR^+$) and capable of in vitro self-renewal and differentiation to members of at least the erythroid, myeloid, and megakaryocytic lineages, is obtained by separating the population from a cellular mixture, for example by cytometric cell sorting techniques. Also disclosed is a method of obtaining persistent maintenance of grafted human hematopoietic cells in a mammal, which includes grafting a mammal in utero with a cellular composition enriched in human hematopoietic cells characterized as $CD34^+$, $HLA-DR^-$ and capable of in vitro self-renewal and differentiation to members of the lymphoid, myeloid, erythroid and megakaryocytic lineages.

5 Claims, 5 Drawing Sheets

HUMAN STEM CELL COMPOSITIONS AND METHODS

REFERENCE TO RELATED APPLICATION

This is a continuation-in-part of U.S. Pat. application Ser. No. 07/919,447 filed Jul. 27, 1992, now abandoned, which is hereby incorporated by reference in its entirety.

This application was made with government support under the National Institutes of Health grants R01 CA45279 entitled, "Purification of Primitive Hematopoietic Progenitor Cells" and R01 HL46548 entitled "In Vitro Reconstitution of Normal Human Hematopoiesis". The government has certain rights in this invention.

BACKGROUND

The present invention relates to pluripotent hematopoietic stems cells (PHSC's) and to methods for their isolation and use.

Evidence shows that PHSC's are responsible for the generation of all of the formed elements of blood, including for instance the myeloid, lymphoid, erythroid and megakaryocytic lineages. However, despite this understanding and continued extensive efforts in industry and academia, PHSC's have not been identified and isolated in a pure form.

The high level interest in purifying stem cells speaks to the utility that will be found with enriched stem cell compositions. For example, availability of pure or substantially pure stem cells will provide a means to identify factors which cause or prevent dedication to specific lineages. Pure or substantially pure stem cells may also be used in grafts or transplantations (including autotransplants, allogeneic transplants and others), for example to provide immediate and/or long term health benefits due to the presence and maintenance of the graft or transplant in the host, to provide chimeras, etc. For example, human stem cells may be isolated and used as stem cell grafts for in utero transplantation into human fetuses diagnosed with a genetic disorder which can be corrected by normal BM transplantation. The known similar methods utilize human fetal liver cells as grafts which in most all cases would be from unrelated mismatched donors and in most instances not available at will. Autotransplants of pure stem dells could be potentially useful in several leukemias where purified stem cells could be devoid of cancer cells and might therefore provide a disease-free graft.

Enriched stem cell compositions also represent excellent targets for gene transfer studies and in gene therapy in which cells are genetically manipulated, e.g. by transfection and transduction. In this manner, propagation of a gene introduced or altered by the genetic manipulation in progeny cells can be assured by the cells' capacity for self-renewal. Stem cell compositions may also be used in treating and in research for treating neoplastic conditions such as leukemias, lymphomas, and others.

Researchers in the area have employed various approaches to enrich for stem cells, which are highly rare and currently believed to represent approximately 0.01 to 0.05%. of human bone marrow cells. Schemes to enrich for stem cells have often attempted to selectively isolate cells lacking markers known to exist on differentiated hematopoietic lineages, but having markers known to exist on stem cells. Thus, both negative and positive selection procedures have been employed. The presence of stem cells in the isolated cell fractions is then demonstrated by assessing their capacity to self-renew and differentiate to the various blood cell lineages.

The use of labeled monoclonal antibodies and flow cytometric cell sorting to isolate fractions enriched in stem cells has been successful to a limited degree. Due to the availability of a large number of monoclonal antibodies which can be used for this purpose, none of which directly have identified stem cells, many combinations of antibodies can be employed. Still, by these previous efforts, cells which possess one or more of the functional characteristics attributed to stem cells, but not all, have been obtained.

Various other methods for enriching, isolating and purifying human stem cells have also been generally applied in the fields of experimental hematology and clinical medicine. Examples of such methodologies include counterflow centrifugal elutriation, immunomagnetic separation, panning, and the use of the avidin-biotin interaction over different matrices. Although each of these methodologies has been successful to a limited degree, they have all failed to isolate cells that could be phenotypically characterized as more than just $CD34^+$ cells.

In light of this and other extensive background in the area, there remain needs for new PHSC-enriched compositions and methods for obtaining them. Needs also exist for methods for grafting hosts with PHSC-containing compositions whereby the grafted cells are maintained and differentiated in the host. The present invention addresses these and other needs.

SUMMARY OF THE INVENTION

One preferred embodiment of the invention provides a human-PHSC containing cellular composition comprising a substantially homogeneous population of human hematopoietic cells characterized as $CD34^+$, $HLA-DR^-$, and c-Kit receptor positive ($KR^+$) and capable of in vitro self-renewal and differentiation to members of at least the erythroid, myeloid, and megakaryocytic lineages.

Another preferred embodiment of the invention provides a method for recovering a human-PHSC enriched cell fraction from its mixture with committed progenitors and dedicated lineages thereof, the cell fraction being capable of in vitro self-renewal and differentiation to members of at least the erythroid, myeloid and megakaryocytic lineages. The method includes the step of separating from the cellular mixture a substantially homogeneous population of human hematopoietic cells characterized as $CD34^+$, $HLA-DR^-$, $KR^+$. This may be conveniently accomplished by treating the cellular mixture by counterflow centrifugal elutriation to obtain a first cell fraction enriched, e.g. 2-fold or more enriched, in $CD34^+$, $HLA-DR^-$ cells as compared to the cellular mixture, combining the first fraction with fluorochrome-labeled antibodies to markers including CD34, HLA-DR, and KR, each of said fluorochromes differing from the other, and recovering the substantially homogeneous $CD34^+$, $HLA-DR^-$, $KR^+$ population by means of the fluorochromes, e.g. by cytometric cell sorting techniques. In this regard, sorting as to a specific marker can be done in an individual operation, or sorting as to some or all of the markers can be simultaneously accomplished.

Another preferred embodiment of the invention provides a human-PHSC containing cellular composition comprising a substantially homogeneous population of human hematopoietic cells isolated from human peripheral blood, characterized as $CD34^+$, $HLA-DR^-$ and capable of in vitro self-renewal and differentiation to members of the at least the erythroid, myeloid, and megakaryocytic lineages. Such cell populations have proven to initiate long term cell cultures in a fashion similar to that observed in cultures initiated using their counterpart cells isolated from bone marrow. Preferred populations of this embodiment are characterized as substantially CD34$^+$, HLA-DR$^-$, KR$^+$.

Another preferred embodiment of the invention provides a method for obtaining a human-PHSC enriched cell population capable of in vitro self-renewal and differentiation to members of at least the erythroid, myeloid and megakaryocytic lineages. The method includes the step of separating from peripheral blood a substantially homogeneous population of human hematopoietic cells characterized as CD34$^+$, HLA-DR$^-$. In a preferred mode this method includes the step of mobilizing PHSC's to the peripheral blood, for instance by the administration of suitable agents therefor.

Another preferred embodiment of the invention provides a human-PHSC containing cell population in a culture medium and having an expanded number of cells characterized as CD34$^+$, HLA-DR$^-$. The population is preferably stimulated by a combination of cytokines effective to provide the expansion of the number of CD34$^+$, HLA-DR$^-$ cells.

Another preferred embodiment of the invention relates to a method of obtaining persistent maintenance of grafted human hematopoietic cells in a mammal. The method includes the step of grafting the mammal in utero with a cellular composition enriched in human hematopoietic cells characterized as CD34$^+$, HLA-DR$^-$ and capable of in vitro self-renewal and differentiation to members of the lymphoid, myeloid, erythroid and megakaryocytic lineages. By the method, successful treatments can be obtained, as can chimeras in large animal systems such as ruminant mammals, e.g. sheep, which have bone marrow containing human hematopoietic cells characterized as CD34$^+$ HLA-DR$^-$, and further having peripheral human blood cells characterized as CD45$^+$, CD14$^+$, CD4$^+$, CD8$^+$, CD19$^+$ and CD16/CD56$^+$. These grafted mammals have also shown to be highly persistent in maintaining hematopoietic characteristics of the graft, for example well beyond grafting and birth.

Additional embodiments, features and advantages of the present invention will be apparent from the following description.

DESCRIPTION OF THE PREFERRED EMBODIMENTS

Figure 1:
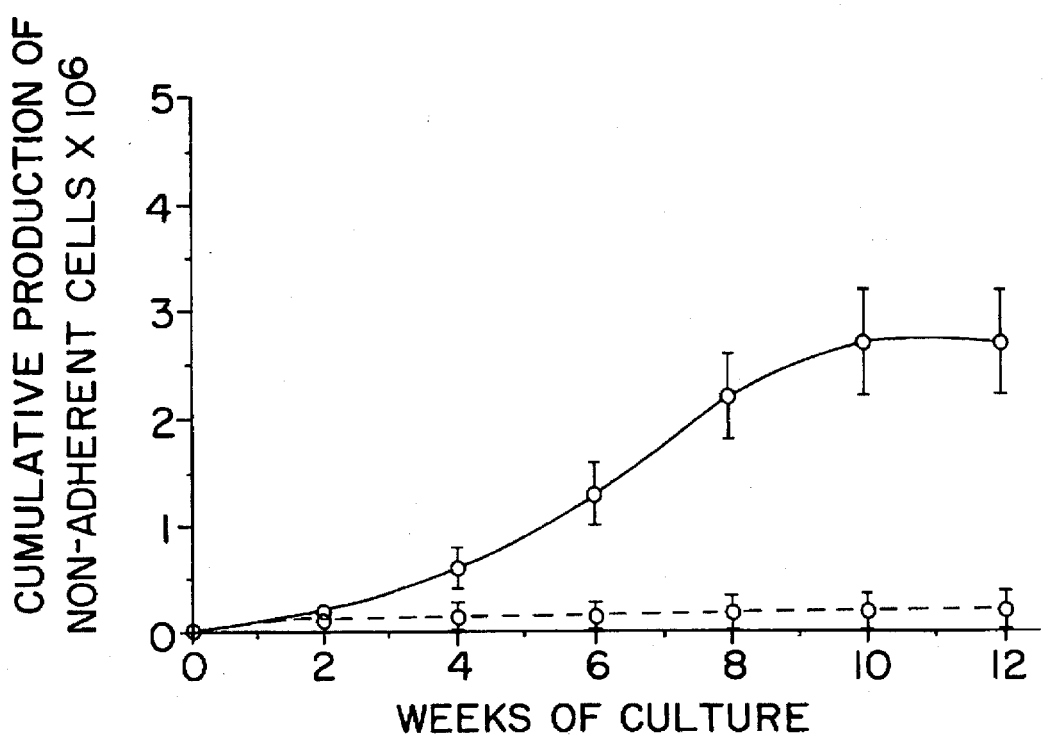
FIG. 1 shows the cumulative production of nonadherent cells per milliliter from two LTBMCs initiated with either (0—0) 1.0×10$^4$ CD34$^+$ HLA-DR$^-$ SR-1$^+$ or (0 - - - 0) 1.0×CD34$^+$ HLA-DR$^-$ SR-1$^-$ cells. Cytokines were added every 48 hours during 12 weeks of LTBMC. Each point represents the cumulative means of corrected LTBMC supernatant counts times 10$^6$±SD tallied at biweekly intervals for 12 weeks and obtained from two separate marrow donors.

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

Human-PHSC containing cellular compositions are provided which include substantially homogenous populations of human hematopoietic cells characterized as CD34$^+$, HLA-DR$^-$, KR$^+$. The CD34$^+$, HLA-DR$^-$, KR$^+$ cells are capable of in vitro self-renewal and differentiation to members of at least the erythroid, myeloid and megakaryocytic lineages. The CD34$^+$, HLA-DR$^-$, KR$^+$ cells are also capable of massive expansion of cell numbers. In addition to the above, preferred populations of the invention are further characterized as CD15$^-$, CD71$^-$ and/or rhodamine 123 dull.

The substantially CD34$^+$ HLA-DR$^-$, KR$^+$ populations may be isolated from their cellular mixtures with committed progenitors and differentiated lineages. For example, the cellular mixture can be adult human bone marrow, umbilical cord blood, fetal liver or peripheral blood.

In an early stage, the cellular mixture is treated so as to substantially remove cells carrying markers associated with dedicated lineages. Preferably, this treatment will result in at least a 2-fold enrichment of cells lacking the mature markers associated with dedicated lineages, more preferably at least 5-fold and most preferably about 10-fold or more. For example, it is preferred to obtain a fraction enriched for $CD34^+$, $HLA-DR^-$ cells in these amounts. This may be accomplished in any suitable manner, for instance by counterflow centrifugal elutriation, soybean agglutination, enrichment with magnetic beads, affinity chromatography over activated matrices, etc. However, the applicants have found it to be highly preferred to accomplish this result by counterflow centrifugal elutriation, and less preferred to use magnetic separation since this latter method does not tend to enrich as highly for $CD34^+$, $HLA-DR^-$ cells.

After the early separation to an enriched fraction as described above, a substantially homogeneous population of $CD34^+$, $HLA-DR^-$, $KR^+$ cells is obtained therefrom. This may be conveniently accomplished by employing an antibody to extracellular portions of KR in conjunction with antibodies to CD34 and HLA-DR, coupled with fluorescence-activated cell sorting.

As an example, the $CD34^+$, $HLA-DR^-$ population of human marrow cells contains the blast colony-forming cell (CFU-B1), the high proliferative potential colony-forming cell (HPP-CFC), and the cell responsible for initiating long-term hematopoiesis in vitro (LTBMC-IC). Further fractionation of the $CD34^+$, $HLA-DR^-$ population based on KR expression (greater than 33% of the $CD34^+$ $DR^-$ cells expressed KR) and utilization of assays for these primitive cells indicated the presence of human PHSC's in the $CD34^+$, $HLA-DR^-$, $KR^+$ fraction. In particular, the $CD34^+$ $HLA-DR^+$, $SR-1^+$ cell population contained the majority of the more differentiated progenitor cells, including the granulocyte-macrophage-colony-forming-unit (CFU-GM); burst-erythroid-forming-unit (BFU-E); CFU-granulocyte, erythrocyte, macrophage, and megakaryocyte; and the CFU-megakaryocyte. By contrast, the $CD34^+$, $HLA-DR^-$, $SR-1^+$ cell population contained fewer of these more differentiated progenitor cells but exclusively contained the more primitive progenitor cells, the BFU-megakaryocyte, HPP-CFC and LTBMC-IC. The overall progenitor cloning efficiency of the $CD34^+$, $HLA-DR^-$, $SR-1^+$ subpopulation was greater than 7%. Both the $CD34^+$, $HLA-DR^-$ and $CD34^+$, $HLA-DR^+$ cell subpopulations lacking KR expression contained few assayable hematopoietic progenitor cells.

Long term bone marrow cultures initiated with $CD34^+$, $HLA-DR^-$, $SR-1^+$ cells generated assayable progenitor cells of at least 2 lineages for 10 weeks, in contrast to $CD34^+$, $HLA-DR^-$, $SR-1^-$ cells which failed to initiate such successful cultures. In these long-term cultures, $CD34^+$, $HLA-DR^-$, $SR-1^+$ cells were capable of massive expansion of cell numbers to over 250-fold as compared to a 10-fold increase by $SR-1^-$ cells. Thus, the applicants have demonstrated that human bone marrow cells which express CD34 and KR but not HLA-DR represent a primitive population of progenitor cells that includes the PHSC.

The invention also provides substantially homogeneous $CD34^+$, $HLA-DR^-$ cell populations isolated from peripheral blood, which have proven to possess advantages in establishing long term cultures as compared to counterpart populations isolated from bone marrow. In particular, long-term hematopoietic cell suspension cultures initiated with $CD34^+$ $HLA-DR^-$ cells isolated from peripheral blood produced greater numbers of total cells and progenitor cells than long-term suspension cultures initiated with $CD34^+$ $HLA-DR^-$ cells obtained from bone marrow. These cell populations can be obtained in accordance with the invention by mobilizing progenitor cells and PHSC's into the peripheral blood and then isolating the desired population from collected peripheral blood by employing, for example, sorting techniques as described herein. The mobilization is advantageously achieved by administering cyclophosphamide to the subject followed by the administration of one or more hematopoietic growth factors, for example interleukin-3 (IL-3)+granulocyte-colony stimulating factor (G-CSF), IL-3+granulocyte-macrophage-colony stimulating factor (GM-CSF) or a recombinant GM-CSF/IL-3 fusion protein.

The invention further provides human PHSC-containing cellular compositions in culture medium in which the number of $CD34^+$, $HLA-DR^-$ cells is expanded. Long term cell cultures of the invention include stimulation by a combination of cytokines effective to provide the expansion of the $CD34^+$, $HLA-DR^-$ cell number, and are preferably initiated by a human-PHSC containing cell population characterized as $CD34^+$, $HLA-DR^-$, $CD15^-$, rhodamine 123 dull ($R^+$). Useful cell populations for such initiations may also be further characterized as $KR^+$ and/or $CD71^-$.

Preferred cell cultures of the invention are maintained by the addition of an effective combination of cytokines including c-kit ligand. For example, preferred cell cultures maintained by the periodic addition of c-kit ligand in combination with the above-mentioned GM-CSF/IL-3 fusion protein, by day 21 after initiation, had a greater than twofold increase in the number of assayable HPP-CFC cells. Further, periodic analysis of cells harvested from these preferred long term cell cultures showed that the number of $CD34^+$, $HLA-DR^-$ cells increased by more than fifty-fold by day 21. Individual HPP-CFC colonies were also serially cloned to examine the in vitro expansion of HPP-CFC. Secondary cloning of individual, day 28 primary HPP-CFC demonstrated that 46% of these colonies formed an average of nine secondary granulocyte-macrophage-colony-forming-unit (CFU-GM) derived colonies, whereas 43% of primary HPP-CFC gave rise to between one and six secondary HPP-CFC colonies and 6 to 26 CFU-GM.

As indicated above, other aspects of the invention provide methods for obtaining persistent maintenance of grafted hematopoietic cells in a mammal. These methods involve grafting a mammal in utero with a cellular composition enriched in human hematopoietic cells characterized as $CD34^+$, $HLA-DR^-$. In this regard, the cellular composition used for the graft may also be one according to the above-described embodiments of the invention. The cellular compositions of the invention will also find use in gene transfer and gene therapy studies, reconstituting irradiated marrow populations, treating neoplastic conditions, to purge bone marrow of neoplastic cells as a means of preparing autologous bone marrow grafts, and other similar applications. The cellular compositions can be maintained in conventional long-term cultures, may be frozen and stored in liquid nitrogen pending later use, etc.

To promote a further understanding of the invention and its preferred embodiments, advantages and features, the following Examples are provided. It will be understood, however, that these Examples are illustrative and not limiting in nature.

EXAMPLE 1

ISOLATION OF PHSC-ENRICHED CELL POPULATIONS AND ESTABLISHMENT OF LONG TERM CELL CULTURES

I. ISOLATION OF $CD34^+$, $HLA-DR^-$, $KR^+$ POPULATIONS FROM BONE MARROW

A. Experimental

Cell Separation:

Human bone marrow (BM) samples were aspirated from the posterior iliac crest of normal volunteers after informed consent was obtained according to the guidelines established by the Human Investigation Committee of the Indiana University School of Medicine. Bone marrow aspirates were immediately diluted 1:1 with Iscove's Modified Dulbecco's Media (IMDM: GIBCO Laboratories, Life technologies, Inc. Grand Island, N.Y.) containing 20 U sodium-heparin/mL. Low density mononuclear cells (LDMC) were isolated by density centrifugation of the heparinized marrow layered over Ficoll-Paque (Pharmacia Fine Chemicals, Piscataway, N.J.) at 750 g. LDMC cells were suspended in phosphate buffered saline (PBS), pH 7.4, containing 5% fetal calf serum, 0.01% EDTA wt/vol., and 1.0 g/l D-glucose, and injected into a Beckman counterflow centrifugal elutriation (CCE) system at 10° C. at a rotor speed of 1,950 rpm using a JA-17 rotor and standard separation chamber (Beckman Instruments, Inc., Palo Alto Calif.). Effluent samples eluting at flow rates between 12 and 14 mL/min (FR 12–14; presort) were collected as previously described by Brandt et al., *J. Clin. Invest.*, Vol. 82, p. 1017 (1988). The FR 12–14 cell population contained greater than 70% of progenitor cells and was used in subsequent steps.

MoAbs

The following three purified mouse antihuman (m α h) MoAbs were used as immunologic probes for cell sorting experiments: (1) m α h CD34.IgG$_1$ (Becton Dickinson Immunocytometry Systems, Mountain View, Calif.); (2) m α h HLA-DR conjugated with phycoerythrin (HLA-DR*PE). IgG$_{2a}$ (Becton Dickinson); (3) m α h SR-i. IgG$_{2a}$ (see Broudy et al., *Blood*, Vol. 79, p. 338 (1992)). In addition, m α h MoAbs to CD15, and CD71 were used as described by Brandt et al., *J. Clin. Invest*, Vol. 86, p. 932 (1990). The supravital mitochondrial membrane specific dye rhodamine 123 ($R^{123}$) was used as previously described by Srour et al., *Cytometry*, 12, 179 (1991).

Cell Labeling Techniques

FR 12–14 cells were centrifuged at 750 g to obtain a pellet to which 1 μg m α h CD34/$10^6$ FR 12–14 cells and 1 μg SR-1/$10^6$ FR 12–14 cells were added for 20 minutes of incubation at 4° C. Control FR 12–14 cells were incubated with 1 μg mouse IgG 1/$10^6$ FR 12–14 cells and 1 μg mouse IgG$_{2a}$/$10^6$ FR 12–14 cells concurrently.

FR 12–14 cells were washed with 1% wt/vol bovine serum albumin (BSA; Calbiochem Corporation, La Jolla, Calif.) in phosphate-buffered saline (PBS). Both 1 μg goat antimouse (g α m) IgG$_1$ conjugated with Texas Red (TR; Southern Biotechnology Associates, Inc., Birmingham, Ala.)/$10^6$ FR 12–14 cells and 1 μg α m IgG$_{2a}$ conjugated with fluorescein isothiocyanate (FITC; Southern Biotechnology)/$10^6$ FR 12–14 cells were added concurrently to both experimental and control cell samples for 20 minutes of incubation at 4° C.

FR 12–14 cells were washed with 1% wt/vol BSA/PBS and $10^6$ mouse serum (Sigma Chemical Company, St Louis, Mo.)/$10^6$ FR 12–14 cells were added to both experimental and control cell samples for 10 minutes to block any free binding sites on the two g α m second-step antibodies.

One microgram of HLA-DR*PE/$10^6$ FR 12–14 cells was added for 20 minutes of incubation at 4° C. to experimental cells while 1 μg mouse IgG$_{2a}$*PE (Becton Dickinson)/$10^6$ FR 12–14 cells was added to control cells.

Cells were washed with 1% wt/vol BSA/PBS and resuspended in this same buffer at a concentration of $10^7$/mL.

Cell Sorting Techniques

Cells were sorted on a Coulter Epics 753 dual laser flow cytometry system (Coulter Electronics, Hialeah, Fla.). Sorting gates were established for both forward angle light scatter (FALS) and TR fluorescence-positive events (CD34$^+$). A dual-parameter histogram displaying FITC (SR-1) and phycoerythrin (PE) (HLA-DR) fluorescence was then generated from gated CD34$^+$ events. Using this gated histogram, sorting windows were established for both positive and negative FITC and PE fluorescence. This gating procedure allowed for the isolation of four different cell populations: CD34$^+$ HLA-DR$^-$ SR-1$^-$; CD34$^+$ HLA-DR$^+$ SR-1$^+$; CD34$^+$ HLA-DR$^+$ SR-1$^-$; and CD34$^+$ HLA-DR$^-$ SR-1$^+$. The phenotypic purity of all four populations as determined by postsort flow cytometric analysis exceeded 95%. Additional useful cell populations of the invention, in addition to the above being further characterized as CD15$^-$, CD71$^-$, and or $R^{123}$ dull, are analogously obtained using the appropriate antibodies and known procedures (see e.g. Brandt et al., *J. Clin. Invest.*, Vol. 86, p. 932 (1990)).

The cells from each population were classified by performing differential cells counts on Wright-Giemsa-stained cytocentrifuge cell preparation using established morphologic criteria. Each population of cells was also assayed for various classes of human hematopoietic progenitor cells using procedures described below.

Recombinant Human Hematopoietic Cytokines

The following three purified recombinant human hematopoietic cytokines were used as colony-stimulating factors in these experiments: (1) interleukin-3 (IL-3): specific activity (sp act) $1.0 \times 10^8$ U/mg protein determined from mixed colony formation by human BM cells (Genzyme Corporation, Boston, Mass.); (2) KL: sp act $1.0 \times 10^5$ U/mg protein determined by proliferative effects on MC6 cells (Immunex Corporation, Seattle, Wash.); (3) erythropoietin (EPO): sp act $1.0 \times 10^4$ U/mg protein after formulation in BSA as determined by the exhypoxic polycythemic mouse assay (Amgen Biologicals, Thousand Oaks, Calif.); (4) granulocyte-macrophage colony-stimulating factor (GM-CSF): sp act $5.0 \times 10^7$ U/mg protein determined by granulocyte-macrophage colony formation from human BM cells (Genzyme); (5) GM-CSF:IL-3 fusion protein (FP): sp act $2.0 \times 10^9$ U/mg protein determined by proliferative effects on AML193 cells (Immunex Corporation).

LTBMC System

LTBMCs lacking preestablished stromal cell layers were initiated and maintained as described in Brandt et al., *J. Clin, Invest.*, Vol. 86, p. 932 (1990); Brandt et al., *Blood*, Vol. 79, p. 634 (1992); and Briddell et al., *Blood*, Vol 79, p. 332 (1992). Briefly, 35-mm polystyrene tissue culture dishes containing 1 mL IMDM with 10% vol/vol fetal bovine serum (Hyclone, Logan, Utah) were inoculated with $10^4$ of either the CD34$^+$ HLA-DR$^-$ SR-1$^-$ or the CD34$^-$ HLA-DR$^-$ SR-1$^+$ marrow subpopulation obtained after FACS and incubated at 37° C. in 100% humidified 5% CO$_2$ in air. At inoculation, and every 48 hours thereafter, 1 mL cultures received both 1.0 ng IL-3 and 10.0 ng KL. To address the possibility that CD34$^+$ HLA-DR$^-$ SR-1$^-$ cells might be responsive to other cytokines, we established LTBMCs initiated with these cells to which either GM-CSF/KL or FP/KL were added at 48-hour intervals. These two combinations proved to be inferior to the IL-3/KL combination in progenitor cell production and length of viable culture duration from LTBMCs. At weeks 2, 4, 6, 8, 10, and 12, the cultures were demidepopulated by removal of one-half the culture volume, which was replaced with fresh media. Cells in the harvested media were counted, divided, and assayed in both of the subsequently described progenitor cell assay systems.

Progenitor Cell Assay Systems

Serum-containing methylcellulose assay system.

Sorted cells or cells harvested after the demidepopulation of LTBMCs, were assayed for their ability to produce CFU-GM-, BFU-E-, CFU-GEMM-, and HPP-CFC-derived colonies in a serum-containing methylcellulose assay system as described in Brandt et al., *J. Clin, Invest.*, Vol. 82, p. 1017 (1988) and Brandt et al., *J. Clin. Invest.*, Vol. 86, p. 932 (1990) One nanogram of IL-3, 10.0 ng KL, and 250.0 ng Epo/mL culture were used as sources of colony-stimulating activity (CSA). Cultures initiated were incubated for 28 days at 37° C. in 100% humidified 5% $CO_2$ in air. CFU-GM-, BFU-E-, and CFU-GEMM-derived colonies were scored after 14 days, while HPP-CFC-derived colonies were scored after 28 days of culture, according to previously established morphologic criteria (Brandt et al., *J. Clin. Invest.*, Vol. 82, p. 1017 (1988) and Brandt et al., *J. Clin. Invest,*, Vol. 86, p. 932 (1990)) HPP-CFC-derived colonies are defined by both the colony size and time of appearance in culture as previously described (McNiece et al., *Exp. Hematol.*, Vol. 19, p. 226 (1991); Brandt et al., *Blood*, Vol. 79, p. 634 (1992)) Human HPP-CFC have been shown to be capable of self-renewal and differentiation of multiple progenitor cells, indicative of their primitive nature. See, Srour et al., *Blood*, Vol. 78, p. 258a (1991) (abstr., suppl. 1).

Serum-depleted fibrin clot assay system.

Sorted cells or cells obtained from LTBMC were assayed for their ability to produce CFU-MK- or BFU-MK-derived colonies in a serum-depleted fibrin clot assay system as described by Bruno et al., *Exp. Hematol.*, Vol. 16, p. 371 (1988) and Briddell et al., *Blood*, Vol. 79, p. 332 (1992). One nanogram of IL-3 and 10.0 ng KL/mL culture were used as sources of CSA. Cultures initiated were incubated for 14 or 21 days, at 37° C. in 100% humidified 5% $CO_2$ in air, to quantitate CFU-MK- and BFU-MK-derived colonies, respectively. After incubation, fibrin clots were fixed in situ in methanol:acetone (1:3) for 20 minutes, washed with PBS, and air dried.

10E5 monoclonal mouse $IgG_{2a}$ antibodies recognizing the human platelet glycoprotein IIb-IIIa complex were used as immunologic probes for identifying human megakaryocytes (MKs) as described by Coller et al., *J. Lab Clin.*, Vol. 107, p. 384 (1986). 10E5 was subsequently tagged with a polyclonal, affinity-purified., FITC-labeled g α m IgG (H+L) antiserum (Kirkegaard and Perry Laboratories, Inc., Gaithersburg, Md.). The 35-mm petri dishes were inverted, and their bases were completely scanned at 100X, using an inverted microscope with reflected fluorescent light attachment (Olympus Corporation, Lake Success, N.Y.). A CFU-MK-derived colony was defined as a cluster of three or more fluorescent cells. A BFU-MK-derived colony was described by criteria established by Long et al. in *J. Clin. Invest.*, Vol. 76, p. 431 (1985). These colonies appeared in marrow cultures as clusters of greater than or equal to 42 fluorescent cells usually distributed in multiple foci of development. Human CFU-MK-derived colonies are distinguished from human BFU-MK-derived colonies by duration of incubation required for their appearance in vitro (12 days verses 21 days, respectively), colony size 11.2±1.2 cells/colony verses 108.6±4.4 cells/colony, respectively), and foci of development (1.2±0.1 foci/colony verses 2.3±0.4 foci/colony, respectively).

Statistical Analysis

Results are expressed as the mean±SD of data obtained from multiple, separate experiments. Statistical significance was determined using the Student's t-test.

B. Results

Initially, the FR 12–14 cells obtained after CCE were analyzed for expression of CD34, HLA-DR, and KR. Data obtained from these three separate marrow specimens showed that 6.5%±1.4% of these FR 12–14 cells expressed CD34 ($CD34^+$). Flow cytometric analysis of HLA-DR and KR expression by these $CD34^+$ cells demonstrated that nearly 80% of the $CD34^+$ cells expressed HLA-DR ($HLA-DR^+$) while over 50% of the $CD34^+$ cells expressed detectable levels of the KR ($SR-1^+$). Flow cytometric analysis also demonstrated that cells that lacked expression of CD34 were non reactive with SR-1, and that cells that react with SR-1 all expressed CD34. Similar results were obtained upon analysis of marrow cells obtained from two additional donors. The $CD34^+$ cells that expressed HLA-DR and those that lacked the expression of HLA-DR were then analyzed for KR expression. The distribution percentage of the KR on $CD34^+$ $HLA-DR^-$ and $CD34^+$ $HLA-DR^+$ cells on three separate BM specimens are shown in Table 1. More than one-third of the $CD34^+$ $HLA-Dr^-$ cells expressed the KR, whereas more than one-half of the $CD34^+$ $HLA-DR^+$ cells were $SR-1^+$

TABLE 1

Distribution of the KR on $CD34^+$ $HLA-DR^-$ and $CD34^+$ $HLA-DR^+$ Cells

| Population | $SR-1^-$ | $SR-1^+$ |
| --- | --- | --- |
| $CD34^+$ $HLA-DR^{-a,b}$ | 66.4 ± 10.6[c] | 33.6 ± 10.6 |
| $CD34^+$ $HLA-DR^{+a,d}$ | 47.9 ± 12.7 | 52.1 ± 12.7 |

[a]$CD34^+$ cells comprised an average of 6.5% ± 1.4% of FR 12–14 BM cells.
[b]$HLA-DR^-$ cells comprised an average of 31.9% ± 17.9% of the $CD34^+$ cell population.
[c]Each point represent the mean distribution percentage of SR-1 ± SD in either the $CD34^+$ $HLA-DR^-$ or $CD34^+$ $HLA-DR^+$ subpopulation of FR 12–14 BM cells. Flow cytometric cell analysis was performed on three separate marrow specimens.
[d]$HLA-DR^+$ cells comprised an average of 68.1% ± 17.9% of the $CD34^+$ cell population.

A morphologic analysis of the four $CD34^+$ marrow subpopulations from two separate BM donors, fractionated on the basis of HLA-Dr and KR expression, is provided in Table 2. Cell populations expressing the KR ($CD34^+$ $HLA-DR^-$ $SR-1^+$, $CD34^+$ $HLA-DR^+SR-1^+$) largely resembled blast cells. Cell populations not expressing the KR ($CD34^+$ $HLA-DR^-$ $SR-1^-$, $CD34^+$ $HLA-DR^+SR-1^-$) contained more differentiated myeloid elements. There were no observable MK elements present in any of the populations analyzed.

TABLE 2

Cellular Composition of Sorted Cell Populations

| Population | Blasts | Myleo | MM | Band | Seg | Baso | Lymph | Norm | Mo |
| --- | --- | --- | --- | --- | --- | --- | --- | --- | --- |
| $CD34^+$ $HLA-DR^-SR-1^-$ | 5.0 | 6.5 | 4.5 | 4.5 | 20.0 | 1.0 | 3.0 | 18.5 | 37.0 |
| $CD34^+$ $HLA-DR^-SR-1^+$ | 94.0 | 0.5 | 0.0 | 0.0 | 0.0 | 2.0 | 0.5 | 0.0 | 3.0 |
| $CD34^+$ $HLA-DR^+SR-1^-$ | 17.5 | 8.0 | 6.0 | 5.0 | 16.0 | 1.5 | 3.5 | 7.5 | 35.0 |

TABLE 2-continued

Cellular Composition of Sorted Cell Populations

| Population | Blasts | Myleo | MM | Band | Seg | Baso | Lymph | Norm | Mo |
|---|---|---|---|---|---|---|---|---|---|
| CD34+ HLA-DR+SR-1+ | 98.5 | 0.5 | 0.5 | 0.0 | 0.0 | 0.0 | 0.0 | 0.0 | 0.5 |

Each point represents the relative mean percentage of each cell type classified by performing differential cell counts on Wright-Giemsa-stained cytocentrifuge preparations of cells obtained by MoAb labeling and FACS. One hundred cells per slide were classified from two separate experiments. Abbreviations: Blasts, blast cells; Myelo, myelocytes; MM, metamylelocytes; Band, banded neutrophils; Seg, segmented neutrophils; Baso, basophilis; Lymph, lymphocytes; Norm, normalblasts; Mo, monocytes.

Figure 4:
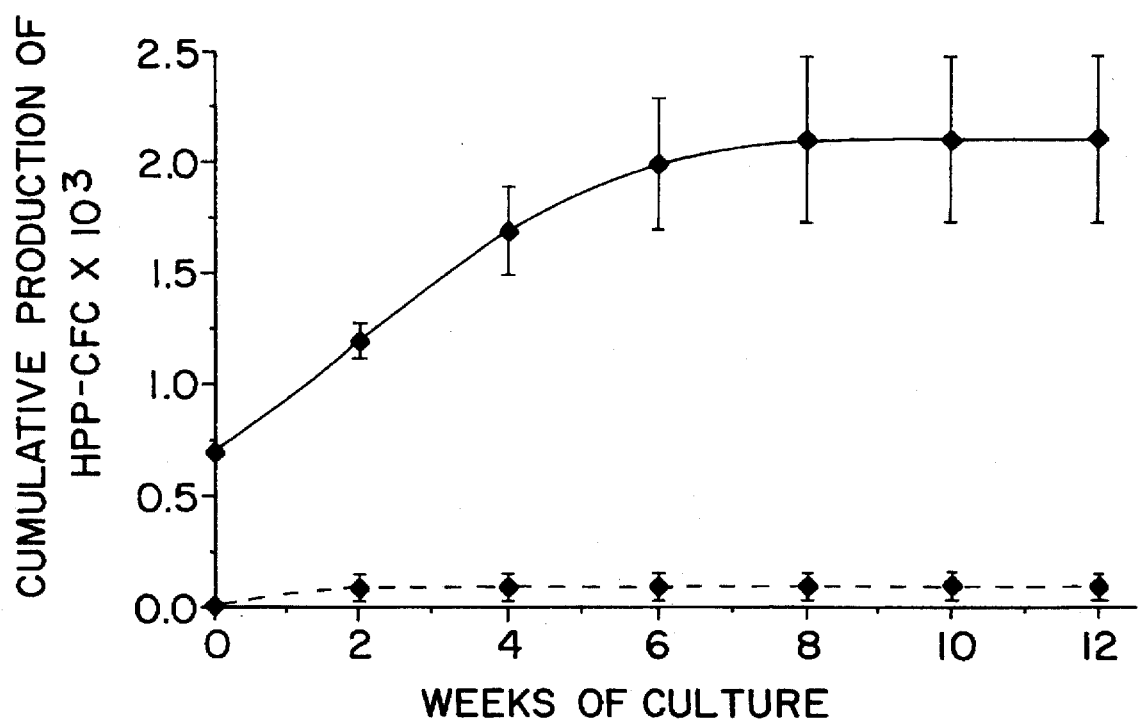
FIG. 4 shows the cumulative production of HPP-CFC per milliliter from two LTBMCs initiated with either (♦—♦) CD34$^+$ HLA-DR$^-$ SR-1$^+$ or (♦ - - - ♦) CD34$^+$ HLA-DR$^-$ SR-1$^-$ cells. Each LTBMC was demidepopulated every 2 weeks and assayed for HPP-CFC in a serum-containing methylcellulose assay system. Each point represents the cumulative mean of corrected HPP-CFC-derived colony counts times 10$^3$±SD obtained from two separate marrow donors.

All four cell populations were directly assayed for hematopoietic progenitor cell enrichment (CFU-GM, BFU-E, CFU-GEMM, CFU-MK, BFU-MK, HPP-CFC). In Table 3, the progenitor cell enrichment of each population is shown. The majority of the most primitive progenitor cells, the FBU-MK and HPP-CFC, were detected in the CD34+ HLA-DR− SR-1+ population. The majority of the more differentiated progenitor cells, the CFU-GM, BFU-E, CFU-GEMM, and CFU-MK, were present in the CD34+ HLA-DR+ SR-1+ cell population. CD34+ HLA-DR+ SR-1+ cells had a cloning efficiency of 31.4% whereas the CD34+ HLA-DR− SR-1+ cell population had an overall 7.3% cloning efficiency. Although the CD34+ HLA-DR+SR-1− cell population contained significant numbers of progenitor cells (16.9% cloning efficiency), the numbers were far less than its SR-1+ counterpart.

whereas CFU-MK generation persisted for 10 weeks. In FIG. 4, the number of assayable HPP-CFC generated during the period of culture is shown. The CD34+ HLA-DR− SR-1+ subpopulation was solely responsible for HPP-CFC production. In fact, the CD34+ HLA-DR- SR-1+-initiated LTBMCs generated nearly a three-fold increase in HPP-CFC numbers over the initial cellular inoculum (708.0±70.0) (FIG. 4)

II. ISOLATION OF CD34+, HLA-DR− POPULATIONS FROM PERIPHERAL BLOOD

A. Experimental

Patient and Treatment Protocol.

Three groups of patients with breast cancer (Groups A, B and C) were involved in this study.

Group A (Table 4) included 6 breast cancer patients who were treated with high-dose chemotherapy followed by

TABLE 3

Hematopoietic Progenitor Cells Present in Various Cell Populations

| | Day 14 | | | | Day 21 | Day 28 |
|---|---|---|---|---|---|---|
| Population | CFU-GM* | BFU-E* | CFU-GEMM* | CFU-MK | BFU-MK† | HPP-CFC* |
| CD34+ HLA-DR−SR-1− | 9.2 ± 3.0 | 3.2 ± 1.0 | 0.5 ± 0.0 | 0.0 ± 10.0 | 5.0 ± 1.0 | 8.2 ± 2.0 |
| CD34+ HLA-DR−SR-1+ | 55.0 ± 5.0 | 24.0 ± 10.0 | 5.2 ± 1.0 | 0.0 ± 0.0 | 22.0 ± 2.0 | 70.8 ± 7.0 |
| CD34+ HLA-DR+SR-1− | 32.8 ± 15.0 | 23.2 ± 10.0 | 2.8 ± 2.0 | 5.0 ± 1.0 | 0.0 ± 0.0 | 5.0 ± 3.5 |
| CD34+ HLA-DR+SR-1+ | 170.0 ± 10.0 | 99.8 ± 4.0 | 29.0 ± 0.5 | 25.0 ± 7.0 | 0.0 ± 0.0 | 12.2 ± 8.0 |

Values are the mean number of derived colonies ± SD of data obtained from duplicate assays performed on two separate occasions.
*Sorted cells were cultured at a concentration of $10^3$/mL in a serum-containing methylcellulose assay system with 1.0 ng IL-3/mL, 10.0 ng KL/mL, and 250.0 ng Epo/mL.
†Sorted cells were cultured at a concentration of $10^4$/mL in a serum-depleted fibrin clot assay system with 1.0 ng IL-3/mL and 10.0 ng KL/mL.

The cellular production of each type of LTBMC (CD34+ HLA-DR− SR-1−, CD34+ HLA-DR− SR-1+) over a 12 week period is shown in FIG. 1. LTBMs initiated with CD34+ HLA-DR− cells expressing the KR produced greater than 25 times the number of cells ($2.5 \times 10^6$) as LTBMCs initiated with cells lacking KR expression ($1.0 \times 10^5$). This number represents a 250-fold increase in cell number when compared with the starting cellular inoculum ($1.0 \times 10^4$) (FIG. 2).

Figure 2:
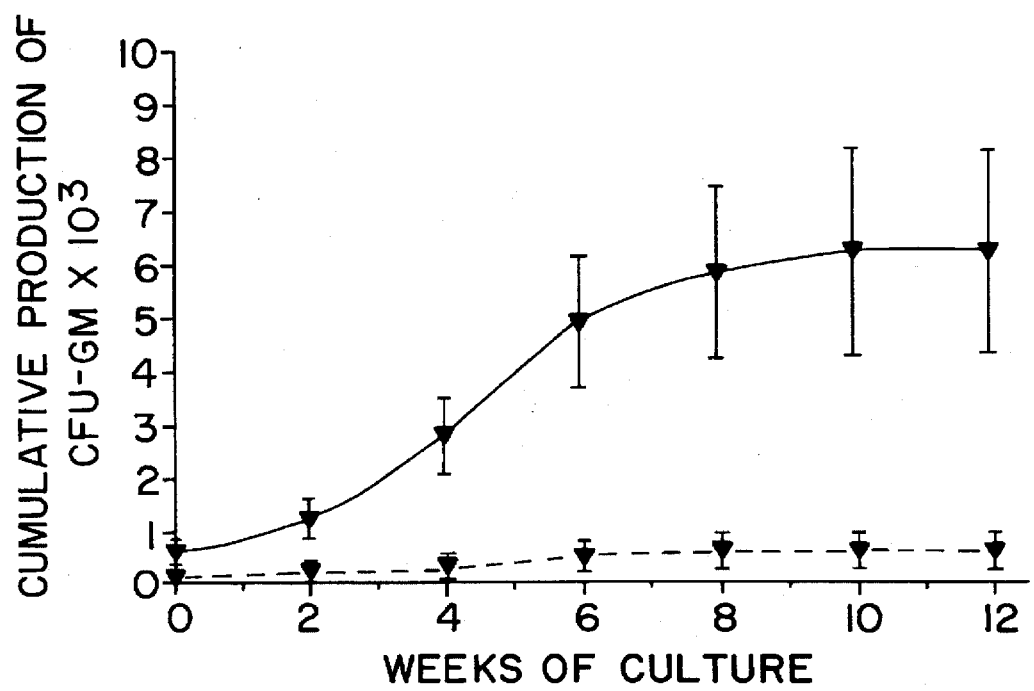
FIG. 2 shows the cumulative production of CFU-GM per milliliter LTBMC from two LTBMCs initiated with either (▼—▼) CD34$^+$ HLA-DR$^-$ SR-1$^+$ or (▼ - - - ▼) CD34$^+$ HLA-DR$^-$ SR-1$^-$ cells. Each LTBMC was demidepopulated every 2 weeks and assayed for CFU-GM in a serum-containing methylcellulose assay system. Each point represents the cumulative mean of corrected CFU-GM-derived colony counts times 10$^3$±SD obtained from two separate marrow donors.
Figure 3A:
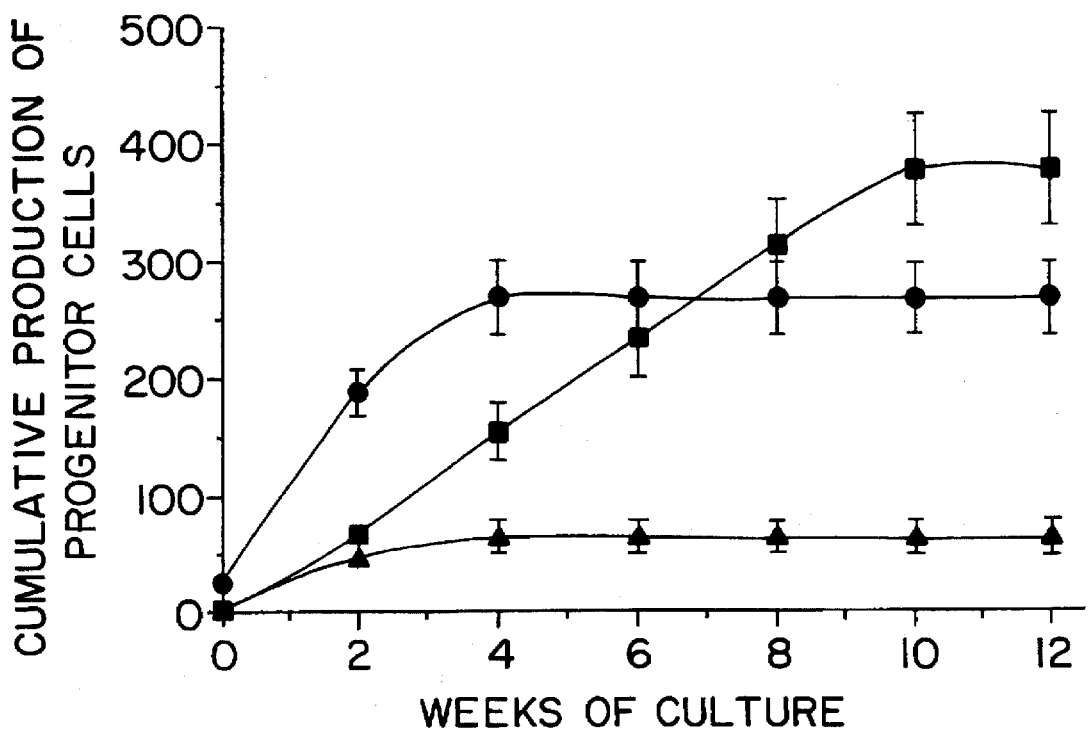
FIG. 3a shows the cumulative production of (●) BFU-E, (▲) CFU=GEMM, and (■) CFU-MK per milliliter from an LTBMC initiated with CD34$^+$ HLA-DR$^-$ SR-1$^+$ cells in LTMBC. The LTBMC was demidepopulated every 2 weeks and assayed for BFU-E and CFU-GEMM in a serum-containing methylcellulose assay system, and for CFU-MK in a serum-depleted fibrin clot assay system. Each point represents the cumulative mean of corrected CFU-E-, CFU-GEMM-, or CFU-MK-derived colony counts±SD obtained from two separate marrow donors.
Figure 3B:
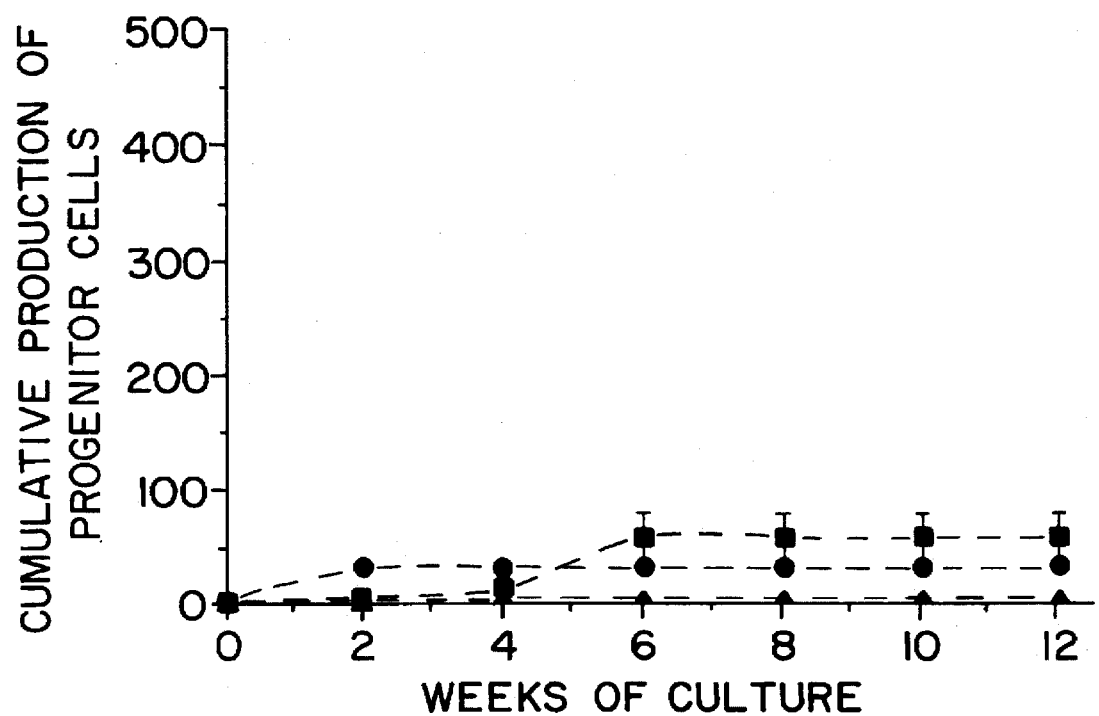
FIG. 3b shows the cumulative production of BFU-E, CFU-GEMM, and CFU-MK per milliliter from an LTBMC initiated with CD34$^+$ HLA-DR$^-$ SR-1$^-$ cells.

The ability of these LTBMCs to produce assayable progenitor cells is shown in FIGS. 2, 3, and 4. The CD34+ HLA-DR− SR-1+-initiated LTBMCs produced greater than $6.0 \times 10^3$ CFU-GM during the period of culture, indicating a greater than 10-fold increase in the number of these progenitor cells from the initial cellular inoculum (550.0±50.0) (FIG. 2). In FIG. 3A and B, progenitor cell production of other lineages is shown for both LTBMCs. Far greater production of BFU-E, CFU-GEMM, and CFU-MK was observed in the LTBMC initiated with CD34+ HLA-DR− SR-1+ cells (FIG. 3A and B). BFU-E and CFU-GEMM production by these cultures was sustained for 4 weeks, sequential growth factor administration. These protocols were approved by the Committee for Clinical Investigation in the Institute of Medical Science in Milan, Italy and informed consent from these patients was obtained according to guidelines outlined by the Institute of Medical Science in Milan which adheres to the principle of the Declaration of Helsinki. The absence of metastatic disease in each of these 6 patients was determined by morphological analysis of marrow aspirates and biopsies. Cyclophosphamide (HD-CTX) (7 g/m$^2$) was divided into 5 doses and administered intravenously for 1 hour every 3 hours. Beginning on day +1 after HD-CTX, patients were then intravenously given combinations of hematopoietic growth factor(s) (C-HGF) with the dual aim of accelerating marrow recovery and enhancing the circulation of hematopoietic progenitors after HD-CTX-induced pancytopenia. The type of hematopoietic growth factor(s), doses, and schedules for each patient are shown in Table 4. Recombinant human interleukin 3 (rhil-3) was provided by Sandoz, Base, Switzerland; recombinant human granulocyte-macrophage colony stimulating factor (rhgm- CSF) was provided jointly by Sandoz and Schering-Plaugh, Milan, Italy; recombinant human granulocyte-colony stimulating factor (rhg-CSF) was provided by Amgen, Milan, Italy and recombinant GM-CSF/IL-3 fusion protein (PIXY-321) was provided by Immunex Corporation.

Group B included 6 breast cancer patients with identical clinical characteristics to those in Group A who did not enroll in the HD-CTX-C-HGF protocol described above. Informed consent from these patients was obtained according to similar guidelines outlined above.

Group C included 8 breast cancer patients who were treated but not enrolled in the HD-CTX-C-HGF protocol described above. These 8 women had locally advanced (Stage IIIB) or metastatic (Stage IV) breast cancer and had entry hematologic parameters including: an absolute neutrophil count greater than or equal to 2000 cells/mm$^3$, platelet count greater than or equal to 100,000/mm$^3$, hemoglobin concentration greater than or equal to 9 g/dl. These patients may have received adjuvant chemotherapy for breast cancer, but had not received prior chemotherapy for at least 6 months prior to the time of study. Informed consent was also obtained from these patients according to guidelines previously established by the Human Investigations Committee of the Indiana University School of Medicine, which adheres to the principles of the Declaration of Helsinki.

ml) were aspirated from numerous sites of the posterior iliac crest of patients in Group C after informed consent was obtained. Low density mononuclear cells (LDMC) were isolated fromt the leukocyte enriched fractions of PB from Group A and B patients and the BM samples from Group C patients by means of ficoll-hypaque density centrifugation as described above.

Sorting of peripheral blood or bone marrow low-density mononuclear cells (MC).

PB or BM mononuclear cells were further isolated by flow cytometric cell sorting generally as described above. Briefly, PBMC were incubated for 20 minutes at 4° C. with a combination of phycoerythrin (PE)-conjugated mouse-anti-HPCA-2 (CD34) (IgG2a isotype, Becton Dickinson Immunocytometry systems), and fluorescein isothiocyanate (FITC)-conjugated mouse anti-human HLA-DR (IgG1 isotype, Becton Dickinson Immunocytometry systems) to isolate CD34$^+$ HLA-DR$^-$ and CD34$^+$ HLA-DR$^+$ cells. BM MC were incubated for 20 minutes at 4° C. with a combination of phycoerythrin (PE)-conjugated mouse-anti-HPCA-2 (CD34) and fluorescein isothiocyanate (FITC)-conjugated mouse anti-human HLA-DR and the lineage-specific markers CD15 (FITC-anti-human CD15, IgG$_1$ isotype, Becton Dickenson Immunocytometry Systems) to isolate CD34$^+$ HLA-DR$^-$ CD15$^-$ cells. In such a staining protocol it was still possible to obtain CD34$^+$ HLA-DR$^+$

TABLE 4

CLINICAL CHARACTERISTICS OF PATIENTS EVALUATED IN THIS STUDY

| Unique Patient Number | Age (yr)/ Diagnosis | Bone Marrow Involvement | Chemotherapy Before High-Dose Cyclophosphamide | Growth Factor(s) Administered After High-Dose Cyclophosphamide | | | Days of PBMC Collection |
|---|---|---|---|---|---|---|---|
| | | | | Type | Dose (µg/kg/day) | Schedule | |
| ML1 | 31 BC | no | none | IL-3 | 5 | +1 to +14 | +13 |
| | | | | GM-CSF | 2.5 | +1 to +7 | |
| | | | | GM-CSF | 5 | +8 to +13 | |
| ML2 | 34 BC | no | none | IL-3 | 5 | +1 to +14 | +12 |
| | | | | G-CSF | 5 | +8 to +14 | |
| ML3 | 46 BC | no | none | IL-3 | 5 | +1 to +15 | +14 |
| | | | | G-CSF | 5 | +8 to +15 | |
| ML4 | 40 BC | no | none | IL-3 | 5 | +1 to +13 | +12 |
| | | | | GM-CSF | 5 | +8 to +13 | |
| ML5 | 48 BC | no | none | IL-3 | 5 | +1 to +14 | +12 |
| | | | | GM-CSF | 5 | +1 to +14 | |
| ML6 | | no | none | PIXY 321[1] | 5 | +1 to +14 | +12 |

All patients received cancer therapy with high-dose cyclophosphamide on day 0 of study. Thereafter, hematopoietic growth factors were administered by continuous intravenous infusion at the dose and schedule detailed in this table. *In patient 5, rhgm-CSF was escalated by 1 µg/kg every two days up to 5 µg/kg/day. BC — breast cancer.
[1]PIXY 321 - recombinantly engineered GM-CSF and IL-3 fusion.

Peripheral blood (PB) and bone marrow (BM) cell separation techniques.

Peripheral blood (PB) was collected using the methodology described by Sienna et al., *Blood*, Vol. 74, p. 1905 (1989) from patients in Group A (patients ML1, 2, 3, 4 and 6 on day +12, +13, or +14, patient ML5 on day 0 and on day +12) (Table 4) and patients in Group B. The whole blood was erythrocyte depleted by gravity sedimentation with 33% Emagel (Behring, Scoppito, Italy) for 30 minutes at 37° C. and a leukocyte enriched fraction obtained (see, Sienna et al., *Blood*, Vol. 77, p. 400 (1991). The PB was then suspended in 50 ml of Iscove's modified Dulbecco's Medium (IMDM) supplemented with 15-20% of fetal calf serum (FCS). All samples were packaged on ice and processed in within 48 hours from the time of collection. The viability of these cells at the time of study ranged from 92% to 98% as assessed by typan blue exclusion. Small BM samples (1–2 cells even though both HLA-DR and CD15 were FITC conjugated. Cells stained with both markers display two distinct green fluorescence peaks. The "dim" peak corresponding to HLA-DR is between 1 and 1.5 logs less fluorescent than the "bright" peak corresponding to CD15. Simultaneous staining with PE-conjugated CD34; FITC-HLA-DR and FITC-CD15 allows for the detection of CD34$^+$ HLA-DR$^-$ CD15$^-$, CD34$^+$ HLA-DR$^+$ and CD34$^+$ HLA-DR$^-$ CD15$^+$cells. Sorting windows were established to collect CD34$^+$ HLA-DR$^-$ CD15$^-$ and CD34$^+$ HLA-DR$^+$ cells only. Controls consisted of the corresponding isotype matched, nonspecific myeloma proteins used in parallel with the staining monoclonal antibodies. Cells were stained at a concentration of 8×10$^7$/ml and washed in 1% bovine serum albumin (BSA) in PBS. Immediately after staining, cells were sorted on a Coulter Epics 753 dual-laser flow cytometer (Coulter Electronics) equipped with a CICERO high speed computer (Cytomation, Fort Collins, Colo.). FITC and PE were excited using the 488-nm wavelength from a dedicated 5-w argon laser. Cells were first gated on forward-angle light scatter and then sorting windows were established to collect PB CD34$^+$ HLA-DR$^-$ and CD34$^+$ HLA-DR$^+$ cells, or BM CD34$^+$ HLA-DR$^-$ CD15$^-$ and CD34$^+$ HLA-DR$^+$ cells. The CD34$^+$ HLA-DR$^+$ cell population is enriched for differentiated marrow progenitor cells including (CFU-GM), (BFU-E), megakaryocyte-colony-forming-unit (CFU-MK) and granulocyte-erythroid-macrophage-megakaryocyte-colony-forming-unit (CFU-GEMM), while the CD34$^+$ HLA-DR$^-$ or CD34$^+$ HLA-DR$^-$ CD15$^-$ cell populations are enriched for several classes of primitive hematopoietic progenitor cells including blast-colony-forming-unit (CFU-B1), (HPP-CFC), burst-megakaryocyte-forming-unit (BFU-MK) and long-term bone marrow culture-initiating cells (LTBMC-IC).

In 4 patients (2 each from Groups A and B), a multicolor staining protocol was used to also determine c-kit (KR) expression on CD34$^+$ HLA-DR$^-$ cells. The SR-1 antibody to the c-kit receptor was used as described above.

Hematopoietic growth factors.

Recombinant human stem cell factor (SCF, specific activity, 5×10$^5$ U/mg), IL-3 (Specific activity 10$^5$ U/mg) and GM-CSF (specific activity, 10$^7$ U/mg) were obtained from Amgen Inc., Thousand Oaks, Calif. Human urine erythropoietin (Epo, specific activity, 34.8 U/mg) was purchased from Toyobo Co., LTD., Japan Long-term suspension cultures.

Stromal cell-free long-term marrow or PB cultures (LTBMC) or (LTPBC) were initiated and maintained generally as described above. Sorted PB CD34$^+$ HLA-DR$^-$ or BM CD34$^+$ HLA-DR$^-$ CD15$^-$ cells (1×10$^4$/ml) were seeded in flat-bottomed 24-well plates in 1 ml IMDM supplemented with 10% FCS, SCF 100 ng/ml and IL-3 1 ng/ml, and incubated at 37° C. in 100% humidified 5% CO$_2$ in air. Every 48 hours thereafter, cultures received SCF 100 ng/ml and IL-3 1 ng/ml. At weekly intervals, the cultures were demi-depopulated by the removal of half the culture volume which was then replaced by fresh medium and cytokines. Cells in the harvested medium were counted and assayed for CFU-GM and BFU-E.

Hematopoietic progenitor cell assays.

Freshly sorted PB or BM CD34$^+$ HLA-DR$^+$ and CD34$^+$ HLA-DR$^-$ cells (1×10$^3$/ml) and cellular aliquots obtained from LTPBC or LTBMC (1×10$^4$/ml) were suspended in 34-mm plastic tissue culture dishes (Costar Data Packing, Cambridge, Me.) containing 1 ml of 30% FCS, 5×10$^{-5}$M 2-mercaptoethanol, 1 U human urine Epo, 100 ng/ml SCF, 1 ng/ml IL-3, 200 pg/ml GM-CSF and 1.1% methylcellulose in IMDM. The cultures were incubated at 37° C. in 100% humidified 5% CO$_2$ in air. After 14 days, CFU-GM, BFU-E and CFU-GEMM colonies yielded by CD34$^+$ HLA-DR$^+$ cells, or after 28 days HPP-CFC colonies yielded by CD34$^+$ HLA-DR$^-$ cells were enumerated in situ using an inverted microscope and standard criteria for their identification.

BFU-MK and CFU-MK were assayed in a serum-depleted assay system detailed by Briddell et al. in *Blood*, Vol. 79, p. 3159 (1992). The BFU-MK assay was initiated with either 5×10$^3$/ml of PB CD34$^+$ HLA-DR$^-$ or BM CD34$^+$ HLA-DR$^-$ CD15$^-$ cells while the CFU-MK assay was initiated with 5×10$^3$/ml of PB or BM CD34$^+$ HLA-DR$^+$ cells. Freshly sorted cells were suspended in a 1 ml serum-depleted fibrin clot containing 100 ng/ml SCF and 1 ng/ml IL-3 and incubated at 37° C. in a 100% humidified atmosphere containing 5% CO$_2$ in air. After 12 days (for CFU-MK) and 21 days (for BFU-MK), the cultures were fixed in situ and stained using 10E5 mouse monoclonal IgG antibodies recognizing platelet glycoproteins IIb–IIIa complex (provided by Dr..Barry S. Coller State University of New York-Stoney Brook, N.Y.) and a fluorescein-labeled, affinity-purified goat anti-mouse IgG (H+L) (Kirkegaard and Perry Laboratories). BFU-MK or CFU-MK colonies were enumerated utilizing an epifluorescent microscope according to established criteria (see, Briddell et al., *Blood*, Vol. 79, p. 3159 (1992)).

Statistical analysis.

The results expressed as the mean±SEM were obtained from duplicate experiments. Statistical significance was determined using the Mann-Whitney U test.

B. Results

The hematopoietic progenitor cells (HPC) and PHSC content of various PB and BM cell subpopulations was initially assessed by monitoring cell phenotypes. The number of CD34$^+$ cells/ml was used as a measure of both HPC and HSC content in a particular cell population while CD34$^+$ HLA-DR$^+$/ml was utilized to quantitate HPC numbers and the numbers of CD34$^+$ HLA-DR$^-$/ml and/or CD34$^+$ HLA-DR$^-$ SR-1$^+$/ml served as a means of quantitating changes in PHSC numbers (Table 5). If one compares the phenotype of PBMC's present in Group A to the phenotype of PB MC's in Group B patients, it is readily observed that Group A PBMCs have remarkably greater numbers of CD34$^+$, CD34$^+$ HLA-DR$^+$, CD34$^+$ HLA-DR$^-$ and CD34$^+$ HLA-DR$^-$ SR-1$^+$ cells/ml of PB. These data were quantitated in this fashion in order to correct for any changes in PB cellularity that HD-CTX+HGF administration might produce. From 21- to 150-fold greater numbers of CD34$^+$ cells were observed in Group A PBMC than Group B PBMC while, 20- to 228-fold greater numbers of CD34$^+$ HLA-DR$^+$ cells as well as 15- to 930-fold greater numbers of CD34$^+$ HLA-DR$^-$ cells were observed (Group A v. Group B) (Table 5). No CD34$^+$ HLA-DR$^-$ SR-1$^+$ cells were detected in the PB obtained from Group B patients (Table 5). In contrast, 13.0±9.2×10$^3$/ml of CD34$^+$ HLA-DR$^-$ SR-1$^+$ cells were present in the PB following HD-CTX+C-HGF (Group A) (Table 5). The frequency of CD34$^+$, CD34$^+$ HLA-DR$^+$ and CD34$^+$ HLA-DR$^-$ cells in Group A PBMCs was comparable to that present in BM aspirated from breast cancer patients (Group C) (Table 5).

TABLE 5

Phenotypical analysis of peripheral blood and bone marrow mononuclear cells obtained from patients with breast cancer.

| | Absolute number of cells ($\times 10^3$/ml) | | | | |
|---|---|---|---|---|---|
| UPN[1] | $CD34^{+2}$ | $CD34^{+2}$ HLA-DR$^+$ | $CD34^{+2}$ HLA-DR$^-$ | $CD34^{+2}$ HLA-DR$^-$ CD15$^-$ | $CD34^{+2}$ HLA-DR$^-$ SR-1$^+$ |
| Group A[3] | | | | | |
| ML1 | 78.6 | 72.0 | 6.6 | ND6 | ND |
| ML2 | 59.4 | 55.0 | 4.4 | ND | ND |
| ML3 | 140.4 | 136.0 | 4.4 | ND | ND |
| ML4 | 116.4 | 112.0 | 4.4 | ND | 3.7 |
| ML5 | 289.4 | 228.0 | 61.4 | ND | ND |
| ML6 | 71.0 | 40.0 | 31.0 | ND | 22.0 |
| Mean ± SEM | 125.6 ± 34.8* | 107.9 ± 28.2* | 19.0 ± 9.5* | | 13.0 ± 9.2* |
| Group B[4] | | | | | |
| ML7 | 1.7 | 1.6 | 0.1 | ND | ND |
| ML8 | 2.5 | 2.5 | 0.0 | ND | ND |
| ML9 | 3.7 | 3.5 | 0.2 | ND | ND |
| ML10 | 3.5 | 3.2 | 0.3 | ND | ND |
| ML11 | 2.7 | 2.7 | 0.0 | ND | 0.0 |
| ML12 | 4.4 | 3.5 | 0.9 | ND | 0.0 |
| Mean ± SEM | 3.1 ± 0.4 | 2.6 ± 0.4 | 0.2 ± 0.1 | | 0.0 ± 0.0 |
| Group C[5] | | | | | |
| IN1 | 58.6 | ND | ND | 10.0 | ND |
| IN2 | ND | ND | ND | 9.0 | ND |
| IN3 | 234.0 | 178.0 | ND | 56.0 | ND |
| IN4 | 141.0 | 116.0 | ND | 25.0 | ND |
| IN5 | 104.0 | 87.0 | ND | 17.0 | ND |
| IN6 | 85.4 | 82.0 | ND | 3.4 | ND |
| IN7 | 6.9 | 6.6 | ND | 0.3 | ND |
| IN8 | 169.3 | 162.0 | ND | 7.3 | ND |
| Mean ± SEM | 114.2 ± 26.8# | 105.0 ± 25.0# | | 16.0 ± 6.3# | |

[1] UPN — Unique Patient Number. ML — Milan. IN — Indianapolis.
[2] The number of CD34$^+$, CD34$^+$ DR or CD34$^+$ DR$^-$ or CD34$^+$ DR$^-$ SR-1$^+$ cells/ml of PB or BM was calculated by the following formula:

$$\text{Absolute cell number} = \frac{\text{Percentage of cells with particular phenotype} \times \text{number of low-density monouclear cells}}{\text{Total volume of peripheral blood or bone marrow aspirated}} \times \text{Total}$$

[3] PB cells from breast cancer patients treated with HD-CTX and growth factors in Milan.
[4] PB cells from breast cancer patients in Milan not enrolled in HD-CTX and growth factors administration protocol.
[5] BM cells from breast cancer patients in Indianpolis not treated with HD-CTX and growth factors.
[6] ND — not determined
*p value < 0.01 when compared to Group B
p value > 0.05 when compared to Group A The number of assayable HPC present in PBMC following HD-CTX+C-HGF (Group A) was also compared to PBMCs collected from a comparable patient population not receiving this therapy (Group B). HD-CTX+C-HGF administration resulted in a statistically significant greater number of circulating CFU-GM (p less than 0.01), BFU-E (p less than 0.01), CFU-GEMM (p less than 0.01) and CFU-MK (p less than 0.01) (Group A vs. Group B) (Table 6).

Furthermore, HD-CTX+C-HGF administration lead to a mobilization of BFU-MK (Table 6). The BFU-MK were readily detected in the PBMC of Group A patients but not Group B patients ($1.3 \pm 0.9 \times 10^2$/ml in Group A vs. $0.0 \pm 0.0$/ml in Group B, p<0.01) (Table 6). The number of CFU-GM, BFU-E, CFU-MK and BFU-MK assayed from PBMC after HD-CTX+C-HGF (Group A) was comparable to the number detected in BM obtained from Group C patients (Table 6). By contrast, greater numbers of CFU-GEMM were present in PBMNC of Group A patients than in the BM of Group C patients (Table 6). In fact, there was a 13-fold greater number of CFU-GEMM numbers present in one ml of PB from Group A patients than in one ml of BM obtained from Group C patients (Table 6). No HPP-CFC were assayable from either the PBMNC of Group A or B patients but were assayed from the marrow obtained from Group C patients (Table 6).

TABLE 6

Hematopoietic progenitor cells present in the peripheral blood or bone marrow of breast cancer patients.

| UPN[1] | Absolute number of colonies (× 10²/ml) | | | | | |
|---|---|---|---|---|---|---|
| | CFU-GM | BFU-E | CFU-GEMM | CFU-MK | HPP-CFC | BFU-MK |
| Group A[2] | | | | | | |
| ML1 | 25.8 | 34.7 | 21.7 | 5.0 | 0.0 | 3.0 |
| ML2 | 9.9 | 15.3 | 7.1 | 5.0 | 0.0 | 0.0 |
| ML3 | 28.6 | 15.0 | 76.2 | 1.6 | 0.0 | 1.4 |
| ML4 | 14.5 | 38.0 | 6.7 | 2.5 | 0.0 | 0.0 |
| ML5 | 26.8 | 25.1 | 22.8 | 3.9 | 0.0 | 2.6 |
| ML6 | 20.5 | 6.7 | 14.6 | 1.4 | 0.0 | 0.8 |
| Mean ± SEM | 21.0 ± 3.1* | 22.5 ± 5.0* | 24.9 ± 10.6* | 3.2 ± 0.9* | 0.0 ± 0.0 | 1.3 ± 0.9* |
| Group B[3] | | | | | | |
| ML11 | 0.0 | 0.3 | 0.08 | 0.0 | 0.0 | 0.0 |
| ML12 | 0.1 | 0.5 | 0.03 | 0.0 | 0.0 | 0.0 |
| Mean ± SEM | 0.07 ± 0.07 | 0.4 ± 0.2 | 0.05 ± 0.04 | 0.0 ± 0.0 | 0.0 ± 0.0 | 0.0 ± 0.0 |
| Group C[+] | | | | | | |
| IN3 | 52.5 | 45.4 | 2.7 | 2.3 | 0.3 | 5.3 |
| IN4 | 0.0 | 0.0 | 0.0 | 0.5 | 0.3 | 1.0 |
| IN5 | 46.1 | 31.3 | 1.7 | 2.0 | 0.0 | 1.2 |
| IN6 | 23.8 | ND[5] | ND | 2.0 | 0.1 | 0.1 |
| IN7 | 1.7 | 3.1 | 0.3 | 0.1 | 0.2 | ND |
| IN8 | 64.8 | 36.5 | 4.9 | 11.0 | 0.1 | 0.7 |
| Mean ± SEM | 31.5 ± 11.1# | 23.3 ± 9.2# | 1.9 ± 0.9& | 2.9 ± 1.7# | 0.2 ± 0.1& | 1.4 ± 0.8# |

CFU-GM, BFU-E and CFU-GEMM were assayed from 1 × 10³ of PB or BM CD34⁺ DR⁺cells/ml and enumerated on day 14. The individual cultures were supplemented with 100 ng/ml SCF, 1 ng/ml IL-3, 200 pg/ml GM-CSF and 1 U/ml Epo. The HPP-CFC were assayed from 1 × 10³ of PB or BM CD34⁺ DR⁻ cells/ml and enumerated on day 28. The individual cultures were supplemented with 100 ng/ml SCF, 1 ng/ml IL-3, 200 pg/ml GM-CSF and 1 U/ml Expo. The CFU-MK and BFU-MK were assayed from 5 × 10³ of PB or BM CD34⁺ DR⁺ (for CFU-MK) or CD34⁺ DR⁻ (for BFU-MK)/ml and enumerated on day 12 (for CFU-MK) and day 21 (for BFU-MK). The individual cultures were supplemented wiht 100 ng/ml SCF and 1 ng/ml IL-3. The absolute number of colonies/ml of PB or BM was calculated as described in the legend of Table 2.
Each point represents mean of duplicate assay.
[1]UPN — Unique Patient Number. ML — Milan. IN — Indianapolis.
[2]PB cells from breast cancer patients treated vith HD-CTX and growth factors in Milan.
[3]PB cells from breast cancer patients in Milan not enrolled in HD-CTX or growth factors treatment protocol.
[4]BM cells from breast cancer patients in Indianapolis not treated with HD-CTX or growth factors.
[5]ND — not determined.
*p value < 0.01 when compared to Group B.
p value > 0.05 when compared to Group A.
&p value < 0.01 when compared to Group A.

Figure 5A:
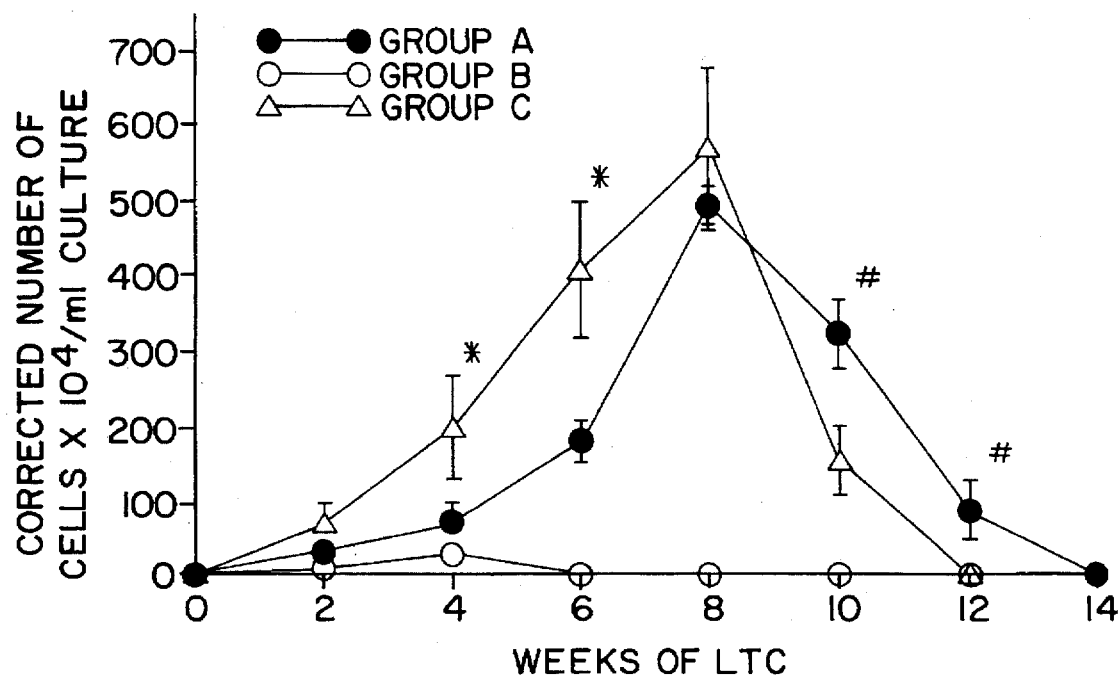
FIG. 5a shows absolute viable cell numbers in stromal cell-free cultures initiated with PB CD34$^+$ HLA-DR$^-$ cells obtained from Group A and Group C patients. Each culture was initiated with 1×10$^4$ cells/ml. Each point represents the mean±SEM of 4 Group A patients, 2 Group B patients and 6 Group C patients.
Figure 5B:
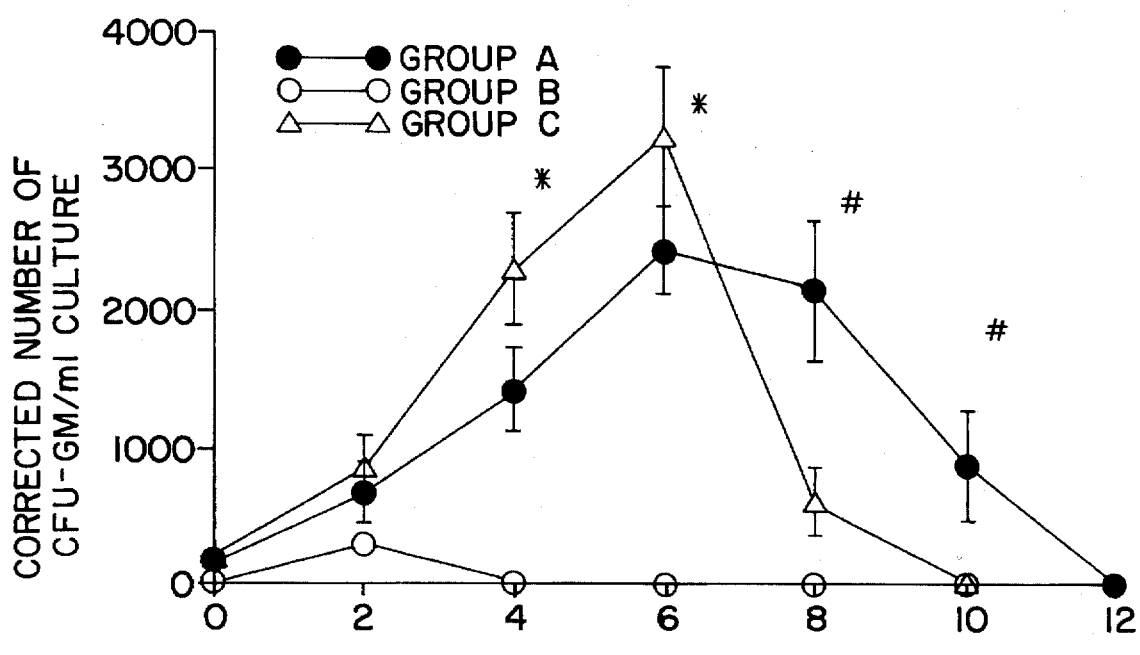
FIG. 5b shows absolute number of CFU-GM in stromal cell-free cultures initiated with PB CD34$^+$ HLA-DR$^-$ cells from Group C patients. Each point represents the mean±SEM of 4 Group A patients, 2 Group B patients and 6 Group C patients.

The ability of PBMC CD34⁺ HLA-DR⁻ cells to initiate and sustain long-term hematopoiesis in vitro was also assessed (FIG. 5a–b; Table 7), CD34⁺ HLA-DR⁻ cells isolated from PBMCs collected from Group B patients were largely incapable of sustaining long-term hematopoiesis in vitro (FIG. 5a–b; Table 7). By contrast, cultures initiated with CD34⁺ HLA-DR⁻ cells isolated from the PBMC of Group A patients were capable of producing viable cells for 12 weeks (FIG. 5a), assayable CFU-GM for an average of 9 weeks (range 8–10 weeks) (FIG. 5b) and BFU-E for an average of 4 weeks (range 2–6 weeks) (Table 7).

If one compares the ability of PB CD34⁺ HLA-DR⁻ CD15⁻ cells in Group C (FIG. 5a–b), one observes that both Group A and Group C CD34⁺ HLA-DR⁻ cells produced peak numbers of cells and CFU-GM on weeks 8 and 6 of culture respectively. PB CD34⁺ HLA-DR⁻ obtained from Group A cells produced substantially greater numbers of CFU-GM on weeks 8 and 10 of culture while Group C LTBMC progenitor cells production had almost entirely ceased by that time. In addition, Group A CD34⁺ HLA-DR⁻ cells lead to a significantly greater cumulative production of CFU-GM in LTPBC (207±56×10²/ml culture) when compared to LTBMC initiated with Group C CD34⁺ HLA-DR⁻ CD15⁻ marrow cells (119±77×10²/ml) (p<0.04).

Long-term erythropoiesis in suspension cultures initiated with PB CD34⁺ HLA-DR⁻ cells from Group A patients was sustained for longer periods of time than in LTPBC or LTBMC initiated with CD34⁺ HLA-DR⁻/CD34⁺ HLA-DR⁻ CD15⁻ cells obtained from patients in either Group B or C (Table 7). Cumulative production of BFU-E during the period of suspension culture was significantly greater when PB CD34⁺ HLA-DR⁻ cells from patients in Group A served as the initiating cell population than when the BM CD34⁺ HLA-DR⁻ CD15⁻ cells from patients in Group C were used to initiate the LTBMC (10.7±5.3×10²/ml cultures vs. 1.5±0.8×10²/ml cultures, p<0.01) (Table 4).

TABLE 7

Total BFU-E production in long-term peripheral blood and marrow suspension cultures.

| | Absolute number of colonies (/ml culture) Weeks of LTC | | | |
|---|---|---|---|---|
| UPN[1] | 0 | 2 | 4 | 6 |
| Group A[2] | | | | |
| ML1 | 570.0 | 584.0 | 741.0 | 793.0 |
| ML2 | 140.0 | 151.0 | 0.0 | 0.0 |
| ML3 | 40.0 | 59.0 | 79.0 | 0.0 |
| ML5 | 208.0 | 328.0 | 428.0 | 0.0 |
| Mean ± SEM | 240.0 ± 115.0 | 281.0 ± 116.0 | 312.0 ± 170.0 | 198.0 ± 198.0 |
| Group B[3] | | | | |
| ML6 | 46.0 | 0.0 | 0.0 | |
| ML7 | 20.0 | 0.0 | 0.0 | |
| Mean ± SEM | 30.0 ± 10.0 | 0.0 ± 0.0 | 0.0 ± 0.0 | |
| Group C[4] | | | | |
| IN2 | 200.0 | 0.0 | 0.0 | |
| IN3 | 700.0 | 204.0 | 0.0 | |
| IN4 | 220.0 | 0.0 | 0.0 | |
| IN5 | 630.0 | 151.0 | 0.0 | |
| IN6 | ND | 45.0 | 0.0 | |
| IN8 | 315.0 | 513.0 | 0.0 | |
| Mean ± SEM | 373.0 ± 130.0 | 152.0 ± 79.0 | 0.0 ± 0.0 | |

Cultures were seeded at $1 \times 10^4$/ml of peripheral blood CD34$^+$ HLA-DR$^-$ or bone marrow CD34$^+$ HLA-DR$^-$ CD15$^-$ cells and supplemented with 100 ng/ml of SCF and 1 ng/ml of IL-3 every 48 hours. Absolute numbers of BFU-E were calculated as described in the legend of Table 2.
[1]UPN — Unique Patient Number. ML — Milan. IN — Indianapolis.
[2]PB cells from breast cancer patients treated with HD-CTX and growth factors in Milan.
[3]PB cells from breast cancer patients in Milan not enrolled in HD-CTX or growth factors treatment.
[4]BM cells from breast cancer patients in Indianapolis not treated with HD-CTX or growth factors.
[5]ND — not determined.

The ability of HD-CTX+C-HGF to mobilize both HPC and PHSC was further confirmed by examining the HPC content of PBMC collected from one patient (ML5, Table 4) both prior to (day 0) and following HD-CTX+C-HGF (day 12). As can be seen in Tables 8 and 9, HD-CTX+C-HGF therapy resulted in a 180-fold increase in the numbers of PBMC CD34$^+$ cells, a 228-fold increase in the numbers in CD34$^+$ HLA-DR$^-$ cells, a 38-fold increase in the numbers of CFU-GM, a 25-fold increase in the numbers of circulating BFU-E, and a 228-fold increase in the numbers of circulating CFU-GEMM (Table 8). In this particular patient, PB CD34$^+$ HLA-DR$^-$ cells were detected only after completion of the mobilization protocol. In addition, PB CFU-MK and BFU-MK were present on day 12 but not on day 0 (Table 8). PB CD34$^+$ HLA-DR$^-$ cells obtained on day 0 did not sustain long-term hematopoiesis in vitro (Table 9). LTPBC initiated with PB CD34$^+$ HLA-DR$^-$ cells isolated on day 12 were capable of producing viable cells for 12 weeks and assayable CFU-GM for 10 weeks and BFU-E for 4 weeks (Table 9). Cohorts of patients in Group A were treated with high-dose cyclophosphamide followed by several different growth factor combinations (patients ML1, 4, 5, IL-3+ GM-CSF; patients ML2, 3, IL-3+G-CSF and patient 6 PIXY-321) (Table 4). There was no significant differences in the effects of these growth factor combinations on the mobilization of HPC and HSC (Tables 5–7).

TABLE 8

Effect of cyclophosphamide and growth factors administration on the mobilization of hematopoietic progenitor cells and stem cells into the peripheral blood of a breast cancer patient.

| | Absolute number of cells ($\times 10^3$/ml PB) | | |
|---|---|---|---|
| | CD34$^+$ | CD34$^+$ HLA-DR$^+$ | CD34$^+$ HLA-DR$^-$ |
| On day 0 | 1.0 | 1.0 | 0.0 |
| On day 12 | 289.4 | 228.0 | 61.4 |

| | Absolute number of colonies ($\times 10^2$/ml PB) | | | | |
|---|---|---|---|---|---|
| | CFU-GM | BFU-E | CFU-GEMM | CFU-MK | BFU-MK |
| On day 0 | 0.7 | 1.0 | 0.1 | 0.0 | 0.0 |
| On day 12 | 26.8 | 25.1 | 22.8 | 3.9 | 2.6 |

The number of CD34$^+$, CD34$^+$ HLA-DR$^+$ or CD34$^+$ HLA-DR$^-$ cells/ml of PB was calculated as described in the legend of Table 2.
CFU-GM, BFU-E and CFU-GEMM were assayed from $1 \times 10^3$ of PB CD34$^+$ DR$^+$ cells/ml and enumerated on day 14. The individual cultures were supplemented with 100 ng/ml SCF, 1 ng/ml IL-3, 200 pg/ml GM-CSF and 1 U/ml Epo. The CFU-MK and BFU-MK were assayed from $5 \times 10^3$ of PB CD34$^+$ HLA-DR$^+$ (for CFU-MK) or CD34$^+$ HLA-DR$^-$ (for BFU-MK)/ml and enumerated on day 12 (for CFU-MK) and day 21 (for BFU-MK).
The individual cultures were supplemented with 100 ng/ml SCF and 1 ng/ml IL-3.
Each point represents mean of duplicate assay.
The absolute number of colonies/ml of PB was calculated as described in the legend of Table 2.

TABLE 9

Long-term suspension cultures initiated with peripheral blood CD34+ HLA-DR− cells obtained prior to and following administration of cyclophosphamide and growth factors.

| | Weeks in long-term culture | | | | | | |
|---|---|---|---|---|---|---|---|
| | 0 | 2 | 4 | 6 | 8 | 10 | 12 |
| Absolute number of cells (× 10⁴/ml culture) | | | | | | | |
| On day 0 | 1.0 | 1.7 | 3.6 | 0.0 | 0.0 | 0.0 | 0.0 |
| On day 12 | 1.0 | 5.0 | 25.0 | 243.0 | 467.0 | 263.0 | 60.0 |
| Absolute number of CFU-GM (/ml culture) | | | | | | | |
| On day 0 | 30.0 | 46.0 | 0.0 | 0.0 | 0.0 | 0.0 | 0.0 |
| On day 12 | 162.0 | 752.0 | 1632.0 | 1831.0 | 3279.0 | 3327.0 | 0.0 |
| Absolute number of BFU-E (/ml culture) | | | | | | | |
| On day 0 | 40.0 | 0.0 | 0.0 | 0.0 | 0.0 | 0.0 | 0.0 |
| On day 12 | 208.0 | 328.0 | 428.0 | 0.0 | 0.0 | 0.0 | 0.0 |

Cultures were seeded at 1 × 10⁴/ml of PB CD34+ HLA-DR− cells and supplemented with 100 ng/ml SCF and 1 ng/ml IL-3 every 48 hours. Absolute cell numbers and numbers of CFU-GM and BFU-E were calculated as described in the legend of Table 2.

III. ESTABLISHMENT OF LONG TERM CELL CULTURES HAVING EXPANDED CD34+, HLA-DR− CELL NUMBER

A. Experimental.

BM cells and cell separation techniques.

BM aspirates were collected in heparinized Iscove's modified Dulbecco's medium (IMDM) from normal healthy volunteers after obtaining informed consent. Low density mononuclear cells were separated over Ficoll-Paque (specific gravity 1.077 g/mL; Pharmacia Fine Chemicals, Piscataway, N.J.). Counterflow centrifugal elutriation of low density BM cells was than performed as described above. Briefly, cells were injected in phosphate-buffered saline (PBS), pH 7.4 containing 5% fetal bovine serum (FBS), 0.01% EDTA wt/vol, and 1.0 g/L D-glucose into an elutriator system with a standard separation chamber (Beckman, Palo Alto, Calif.). Rotor speed and temperature were maintained at 1,950 rpm and 10° C. Fractions elutin at a flow rate of 12 and 14 mL/min (FR 12-14) were collected, pooled, and used for cell staining and sorting.

Immunofluorescence staining and cell sorting.

Monoclonal antibodies CD34 (purified HPCA-1, IgG₁ isotype, and fluorescein isothiocyanate (FITC)-conjugated HPCA-2), CD15 (Leu-M1, IgM isotype), and phycoerythrin (PE)-conjugated HLA-DR (IgG₂ₐ isotype) were obtained from Becton Dickinson Immunocytometry Systems, San Jose, Calif.. FITC-conjugated QBEND 10 (CD34) was obtained from AMAC, Westbrook, Me. R123 and allophycocyanin (APC)-streptavidin were obtained from Molecular Probes, Eugene, Oreg. Texas red (TR)-conjugated goat-anti mouse IgG¹ and biotinylated goat-anti-mouse IgM were obtained from Southern Biotechnology, Birmingham, Ala. Cell staining for four-color flow cytometric cell sorting using R123, PE, TR, and APC was carried out as described by Srour et al., *Cytometry*, Vol. 12, p. 179 (1991). Briefly, cells washed with PBS supplemented with 2% (wt/vol) bovine serum albumin (BSA) were first incubated for 20 minutes with appropriate amounts of CD34 and CD15 simultaneously. Following that, TR-conjugated goat-anti-mouse IgG₁ and biotinylated goat-anti-mouse IgM were added to develop the CD34 and CD15 respectively. Mouse myeloma proteins were then added to block free active sites on the second-step reagents. Finally PE-conjugated HLA-DR, R123 (used at 1 µg/mL) and APC-streptavidine were added together. Cells were then washed with PBS-BSA. Each incubation step was for 20 minutes and the cells were kept at 4° C. in the dark throughout staining and cell sorting. Conjugated and purified isotypematched nonspecific myeloma proteins were used to determine background fluorescence and establish positivity. When R123 was not used in cell staining, FITC-conjugated CD15 (BDIS, San Jose, Calif.) was substituted for purified CD15 in conjunction with PE-conjugated HLA-DR and CD34, which was developed with a TR-conjugated second step reagent.

Cell sorting was performed on a Coulter Epics 753 dual laser flow cytometer (Coulter Corp, Hialeah, Fla.) capable of simultaneously detecting five parameters and equipped with a CICERO high-speed cell sorting computer (Cytomation, Fort Collins, Colo.) Cytometer settings capable of adequately measuring R123 and PE fluorescences simultaneously as well as specifications of optical filters used to separate the four different wavelengths generated from the four fluorochromes were used as previously described. A gating bit map generated on a dual fluorescence (TR/PE) histogram was first constructed to select for CD34+ HLA-DR− cells. This allowed for the generation of a single fluorescence R123 histogram gated on forward angle light scatter, the preestablished CD34+ HLA-DR− gating bit map and CD15 negative events. Two sets of sorting windows were then established in order to divide the CD34+ HLA-DR− CD15− cells into R123$^{dull}$ (R+) and R123$^{bright}$ (R++) subpopulations. Sorted R+ and R++ cells each represented approximately one third of the CD34+ HLA-DR− CD15− events. These selection criteria for R123 were based on the rationale described by Mulder et al., *Exp. Hematol.*, Vol. 15, p. 99 (1987). Cells were sorted at a rate of 3,000 to 4,000 cells per second. Postsort cell viability, as determined by trypan blue exclusion, was always greater than 96%.

DNA analysis.

Staining of cultured cells for cell cycle analysis was performed according to the methodologies of Srour et al., J. Immunol., Vol. 148, p. 817 (1992). Briefly, cells collected from LTBMC were stained with equal volumes of staining buffer (0.1 mg/mL propidium iodide+0.6% Nonidet P-40 in PBS) and 2 mg/mL RNase. The samples were then agitated and kept on ice in the dark for 30 minutes then analyzed on a FACScan flow cytometer calibrated with chicken erythrocytes. For each sample, 5 to 10×10³ cells were analyzed using the SFIT software (BDIS) to determine the percentage of cells in the $G_0+G_1$ ($G_0/G_1$), the S, and the $G_2+M$ phases of the cell cycle. Cultured cells were also stained at different time intervals with FITC-conjugated CD34 (HPCA-2, BDIS, or QBEND10; AMAC) and PE-conjugated HLA-DR and analyzed for expression of these markers on a FACScan flow cytometer.

LTBMC.

Stromal cell-free LTBMC were initiated and maintained using the methodologies described above. Sorted cells were seeded on day 0 at 10⁴ cells/mL in flat-bottomed 24-well plates in IMDM supplemented with 10% fetal calf serum (FCS), and incubated at 100% humidified 5% $CO_2$ in air. At day 0, and every 48 hours thereafter, cultures were fed with 1% BSA/PBS (control group), 10 to 25 ng c-kit ligand, 10 ng fusion protein (FP) (synthetic interleukin-3/granulocyte-macrophage colony-stimulating factor [IL-3/GM]CSF] molecule, P1XY321) or a combination of both. (The c-kit ligand and FP were from Immunex, Seattle, Wash.) At weekly intervals, cultures were demi-depopulated by the removal of half the cultures volume, which was then replaced by fresh medium and cytokines. Cells in the collected media were counted, stained for phenotypic analysis, and assayed for various progenitor cells. Cultures intended for phenotypic and cell cycle analyses only were initiated with 5×10⁴ sorted cells and were terminated after 1 week.

Hematopoietic progenitor cell assays.

Freshly sorted cells from LTBMC were suspended at different cell concentrations in 35-mm tissue culture dishes (Costar Data Packaging, Cambridge, Me.) containing 1 mL of 30% FCS, $5\times10^{-5}$ mol/L 2-mercaptoethanol, 1 U human purified erythropoietin (50 U/mg protein; Toyobo Company Ltd., Osaka, Japan), 10 ng/mL c-kit ligand, 10 ng/ml FP, and 1.1% methylcellulose in IMDM. Cultures were incubated at 37° C. in 100% humidified 5% $CO_2$ in air. Erythropoietic bursts (BFU-E), granulocyte macrophage (CFU-GM), and mixed lineage (CFU-GEMM) colonies were enumerated 14 days later, whereas HPP-CFC-derived colonies were enumerated on day 28.

Cells harvested from LTBMC were assayed for CFU-megakaryocyte (CFU-MK) colonies in a serum-depleted method of Bruno et al., Exp, Hematol., Vol. 16, p. 371 (1988). Cells were suspended in a 1-mL serum-substituted fibrin clot with 100 U IL-3 in 35-mm culture dishes and incubated at 37° C. in a 100% humidified atmosphere containing 5% $CO_2$ in air. Two weeks to 18 days later the cultures were fixed in situ and stained using rabbit anti-human platelet glycoprotein antisera, and FITC-conjugated goat F(ab')$_2$-specific anti-rabbit IgG (Tago, Inc., Burlingame, Calif.). MK colonies were enumerated on a fluorescence microscope and a positive colony was defined as a cluster of three or more fluorescent cells.

Secondary replating of primary HPP-CFC-derived colonies. HPP-CFC colonies growing in semisolid medium were plucked on day 28 from the methylcellulose under direct microscopic visualization using sterile 100 µL glass micropipettes (Drummond Scientific Comany, Broomall, Pa.) and suspended in 200 µL IMDM. The cell suspension was then made up to 1 mL, containing at a final concentration 1.1% methylcellulose, 30% FBS, $5\times10^{-5}$ mol/L 2-mercaptoethanol, 1 U human purified erythropoietin, 10 ng/mL c-kit ligand, and 10 ng/mL FP, which was then transferred entirely into a single well of a 24-well tissue culture plate (Corning Glass Works, Corning, N.Y.). Plates were incubated at 37° C in 100% humidified air with 5% $CO_2$. Secondary CFU-GM- and HPP-CFC-derived colonies were enumerated 14 and 28 days later, respectively, as described above.

B. Results.

$R^+$ cells are enriched for HPP-CFC.

Before using $R^+$ cells for experiments aimed at expanding PHPC into vitro, it was important to establish the HPP-CFC content of BM populations isolated on the basis of their staining with R123. Hematopoietic progenitor cell assays of sorted $R^+$ and $R^{++}$ cells showed that between 9% and 43% of CFU-GM, BFU-E, and CFU-GEMM cloned from CD34$^+$ HLA-DR$^-$CD15$^-$ marrow cells were present in the $R^{++}$ fraction. On the other hand, the majority of assayable HPP-CFC were found in $R^+$ cells (Table 10).

TABLE 10

Colony Formation by Human CD34$^+$ HLA-DR$^-$ CD15$^-$ R$^+$ and CD34$^+$ HLA-DR$^-$ CD15$^-$ R$^{++}$ Cells

| | | Incidence of Progenitors per $1 \times 10^3$ Cells* | | | |
|---|---|---|---|---|---|
| | | Day 14 | | | Day 28 |
| Donor | Cells | BFU-E† | CFU-GM | CFU-GEMM | HPP-CFC |
| 1 | R$^+$ | 31.0 ± 7.6 | 82.2 ± 8.9 | 7.8 ± 1.6 | 9.0 ± 0.8 |
| | R$^{++}$ | 10.0 ± 3.7 | 38.6 ± 4.4 | 1.8 ± 1.8 | 1.5 ± 0.6 |
| 2 | R$^+$ | 21.0 ± 2.8 | 72.0 ± 1.4 | 2.5 ± 0.7 | 4.5 ± 0.7 |
| | R$^{++}$ | 5.5 ± 0.7 | 38.0 ± 2.8 | 0.0 ± 0.0 | 3.0 ± 1.4 |
| 3 | R$^+$ | 7.0 ± 2.8 | 33.7 ± 2.0 | 0.3 ± 0.5 | 2.5 ± 1.7 |

TABLE 10-continued

Colony Formation by Human CD34$^+$ HLA-DR$^-$ CD15$^-$ R$^+$ and CD34$^+$ HLA-DR$^-$ CD15$^-$ R$^{++}$ Cells

| | | Incidence of Progenitors per $1 \times 10^3$ Cells* | | | |
|---|---|---|---|---|---|
| | | Day 14 | | | Day 28 |
| Donor | Cells | BFU-E† | CFU-GM | CFU-GEMM | HPP-CFC |
| | R$^{++}$ | 0.3 ± 0.5 | 3.0 ± 0.8 | 0.0 ± 0.0 | 0.0 ± 0.0 |
| 4 | R$^+$ | 25.0 ± 8.5 | 29.5 ± 5.5 | 1.0 ± 0.0 | 24.0 ± 2.8 |
| | R$^{++}$ | 32.5 ± 0.7 | 7.5 ± 0.7 | 0.5 ± 0.7 | 7.5 ± 2.1 |

*A total of $10^3$ sorted R$^+$ or R$^{++}$ cells were cultured in 35-mm tissue culture dishes containing 1 mL of 30% FCS, $5 \times 10^{-5}$ mol-L 2-mercaptoethanol, 1 U human purified erythropoietin, 10 ng/mL c-kit ligand, 10 ng/mL FP, and 1.1% methylcellulose in IMDM.
†Each point represents the mean ± SD of two (donors 2 and 4), four (donor 3), or five (donor 1) replicates.

Cell and HPP-CFC expansion in LTBMC.

Cellular content as well as numbers of progenitor cells in both $R^+$- and $R^{++}$-initiated LTBMC increased during the culture period, albeit to a different magnitude and at different rates. In response to repeated additions of c-kit ligand and FP, cellular expansion in $R^+$ cultures reached its peak at week 6 with more than a 1,500-fold increase in cell number (Table 11). Under the same conditions, a mere sevenfold increase in cell number at week 3 was observed in $R^{++}$ LTBMC. Only LTBMC initiated with $R^+$ cells continued to produce cells for 10 weeks, indicating that LTBMC-IC were primarily present in the $R^+$ fraction of CD34$^+$ HLA-DR$^-$ CD15$^-$ BM cells.

TABLE 11

Cellular Expansion During LTBMC of R$^+$ and R$^{++}$ Human Marrow Cells

| | Corrected Viable Cell Number* in LTBMC ($\times 10^3$) Days in Culture | | | | | | |
|---|---|---|---|---|---|---|---|
| Cells in LTBMC† | 0 | 14 | 21 | 28 | 42 | 56 | 70 |
| R$^+$ | 10 | 1,200 | 4,300 | 5,800 | 15,700 | 8,200 | 3,600 |
| R$^{++}$ | 10 | ND | 67 | 2 | 0 | 0 | 0 |

This represents data obtained from a single experiment. Similar data were observed in five additional studies.
Abbreviation: ND, not determined.
*Viable cell number = cells/mL culture/(½)$^n$", where n = number of previous demidepopulations.
†Sorted R$^+$ and R$^{++}$ cells were maintained in 1 mL of IMDM containing 10% FCS and were supplemented by the addition of 10 ng/mL FP and 25 ng/mL c-kit ligand every 48 hours.

To monitor the expansion of HPP-CFC during the period of LTBMC, one half of the cells in $R^+$- and $R^{++}$-initiated LTBMC was removed at weekly intervals and assayed for HPP-CFC as well as for CFU-GM- and CFU-MK-derived colonies. LTBMC initiated with $R^{++}$ cells did not contain any assayable CFU-GM, HPP-CFC, or CFU-MK progenitor cells after 3 weeks of culture (Table 12). However, CFU-GM- and CFU-MK-derived colonies continued to be present after 8 weeks in cultures initiated with $R^+$ cells (Table 12). In $R^+$ initiated cultures, HPP-CFC were assayable 4 weeks after the initiation of the cultures but not by week 6. Over a period of 3 weeks, more than a twofold increase in the number of HPP-CFC originally present in the culture at day 0 was detected. Furthermore, there was an overall 5.5-fold increase in HPP-CFC numbers during the entire period of LTBMC. Similar data were observed in two other experiments. However, the degree of HPP-CFC expansion varied among cultures such that one LTBMC initiated with $R^+$ cells resulted in a more than eightfold increase in the number of assayable HPP-CFC at week 3.

TABLE 12

Progenitor Cell Production During LTBMC of $R^+$ and $R^{++}$ Cells

| | Incidence of Progenitors per Culture of* | | | | | |
|---|---|---|---|---|---|---|
| | $R^+$ | | | $R^{++}$ | | |
| Days in Culture† | CFU-GM | CFU-MK | HPP-CFC | CFU-GM | CFU-MK | HPP-CFC |
| 0 | 820 | ND | 90 | 386 | ND | 15 |
| 14 | 5,034 | 56 | 87 | NT | NT | NT |
| 21 | 15,336 | 237 | 216 | 3 | NT | 0 |
| 28 | 4,408 | 174 | 116 | NT | NT | NT |
| 42 | 5,495 | 392 | 0 | NT | NT | NT |
| 56 | 246 | 82 | 0 | NT | NT | NT |
| 70 | 0 | 0 | 0 | NT | NT | NT |

These data represent a single experiment. Similar data were observed in two additional experiments.
Abbreviation: NT, not tested for lack of $R^{++}$ cells at indicated time point.
*Harvested cells at various concentrations were assayed for CFU-GM and HPP-CFC in 35-mm tissue culture dishes as described in Table 1. CFU-GM-derived colonies and HPP-CFC were enumerated on days 14 and 28, respectively, and based on the number of total viable cells per culture from Table 2, the total number of colonies per culture was calculated. The assay of CFU-MK-derived colonies was performed in 1 mL serum-substituted fibrin clot to which $10^5$ cells and 100 U IL-3 were added. Colonies were enumerated after 14 to 18 days of incubation using rabbit anti-human platelet glycoprotein antisera. The number of CFU-MK colonies was corrected to reflect the total number/culture.
†Sorted $R^+$ and $R^{++}$ cells were maintained in 1 mL IMDM containing 10% FCS and were supplemented by the addition of 10 ng/mL FP and 25 ng/mL c-kit ligand every 48 hours.

Expansion of $CD34^+$ $HLA-DR^-$ cells in vitro.

To examine, in an alternative fashion, the capacity of $R^+$ cells to support in vitro expansion of PHPC, the number of cells displaying the original $CD34^+$ $HLA-DR^-$ phenotype was monitored during the period of LTBMC. The loss of CD34 expression or the acquisition of HLA-DR have been shown to occur in differentiating hematopoietic cells in vitro. Results generated from three consecutive weekly analyses of the LTBMC described in Tables 11 and 12 showed that compared with the isotype control, 37% of the cells after 14 days in culture in the presence of c-kit ligand and FP displayed the original $CD34^+$ $HLA-DR^-$ phenotype. The percentage of $CD34^+$ $HLA-DR^-$ cells in these cultures at weeks 3 and 4 decreased to 13% and 2%, respectively. This cell population was undetectable by week 5.

We then determined the absolute number of $CD34^+$ $HLA-DR^-$ cells present in LTBMC at different time points (Table 13). Such calculations showed 44- and 55-fold increases in the number of $CD34^+$ $HLA-DR^-$ cells detected at 2 and 3 weeks of LTBMC, respectively, when compared with the original cell number present at day 0. A rapid and complete decline in the number of $CD34^+$ $HLA-DR^-$ cells occurred by week 6. The presence of assayable HPP-CFC in LTBMC correlated with the presence of $CD34^+$ $HLA-DR^-$ cells in these cultures.

TABLE 13

Number of $CD34^+$ $HLA-DR^-$ Cells Present in $R^+$ LTBMC

| Days in Culture* | Viable Cell Number in LTBMC ($\times 10^3$)† | Percent $CD34^+$ $HLA-DR^-$ Cells in LTBMC‡ | Corrected Number of $CD34^+$ $HLA-DR^-$ Cells in LTBMC ($\times 10^3$)§ |
|---|---|---|---|
| 0 | 10 | 100 | 10 |
| 14 | 1,200 | 37 | 444 |
| 21 | 4,300 | 13 | 559 |
| 28 | 5,800 | 2 | 116 |
| 42 | 15,700 | 0 | 0 |

This represents data from a single experiment. Similar data were obtained in two additional experiments.
*Sorted $R^+$ cells were maintained in 1 mL IMDM containing 10% FCS and were supplemented by the addition of 10 ng/mL FP and 25 ng/mL c-kit ligand every 48 hours.
†Viable cell number = cells/mL culture/$(½)^n$, where n = number of previous demi-depopulations.
‡Percentage of $CD34^+$ $HLA-DR^-$ cells at a given time point was calculated from the flow cytometric analysis of cells in LTBMC shown in FIG. 1.
§Corrected number of $CD34^+$ $HLA-DR^-$ cells at a given time point = (viable cell number in LTBMC $\times$ percent $CD34^+$ $HLA-DR^-$ in LTBMC)/100.

Effect of cytokines on expansion of $CD34^+$ $HLA-DR^-$ cells.

Experiments were performed to examine which cytokines were responsible for the expansion of PHPC in vitro. Because sufficient numbers of $R^+$ and $R^{++}$ cells needed for such studies are difficult to isolate from BM aspirate samples, and R123 fluorescence persists in isolated cells for prolonged periods preventing further accurate flow cytometric analysis, $CD34^+$ $HLA-DR^-$ $CD15^-$ cells were used in these studies. This cell subpopulation was cultured for 7 days in the presence of c-kit ligand and FP, alone or in combination, and cells were then analyzed for CD34 and HLA-DR expression and cell cycle status. Cells exposed to c-kit ligand were considerably smaller than cell cultured in the presence of FP or FP plus c-kit ligand (as measured by forward angle light scatter). In addition, 68% of cells exposed to c-kit ligand expressed CD34 and 75% of these cells remained in $G_0/G_1$. Relative to the cell number at day 0, only a 1.1-fold increase in cell number was detected in these LTBMC. By contrast, 88.5% of cells receiving FP lacked CD34 expression, whereas 42.5% of these cells had exited from $G_0/G_1$, resulting in a 10-fold increase in cell number. Approximately a 15-fold increase cell number was observed in LTBMC receiving c-kit ligand and FP, with 45% of these cells entering into S and $G_2+M$ phases of the cell cycle. This cellular expansion coupled with the fact that 20% of these cells expressed the original $CD34^+$ phenotype indicated that in these cultures, a 2.9-fold increase in the number of $CD34^+$ cells was achieved.

Replating of primary HPP-CFC colonies.

Figure 6:
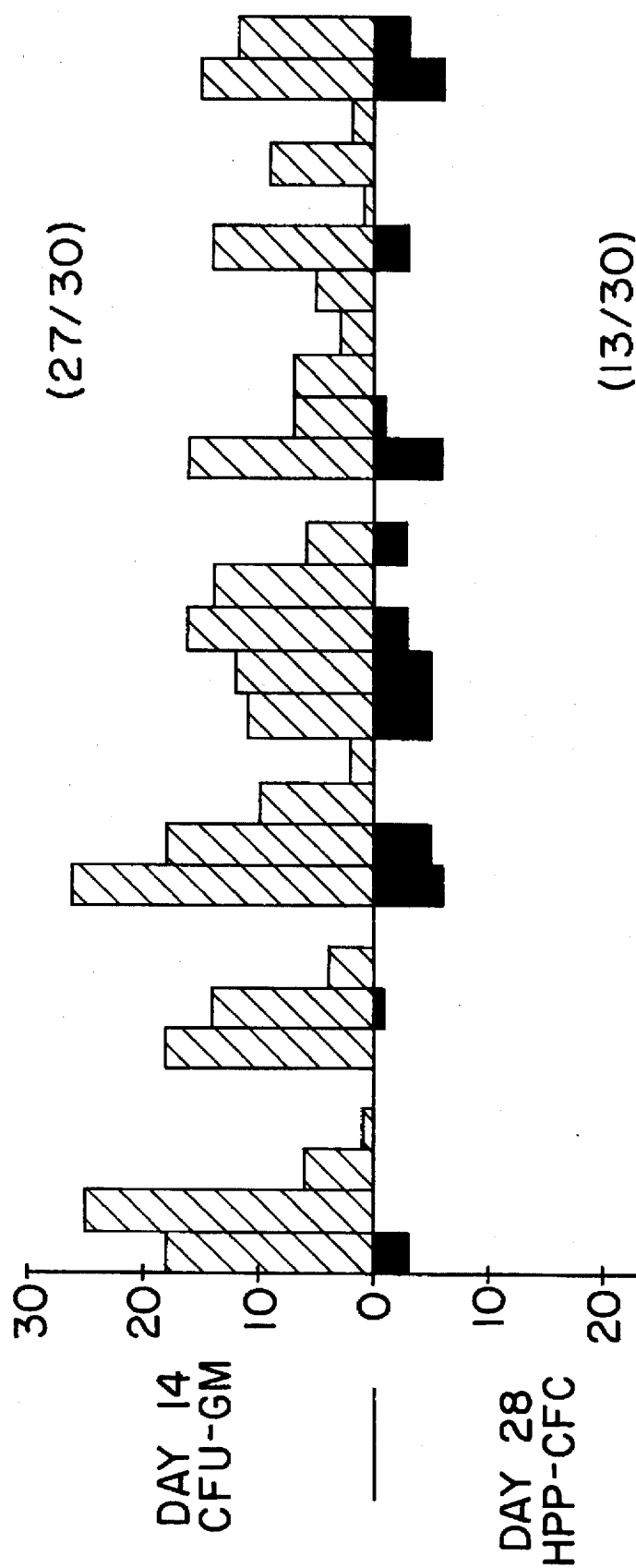
FIG. 6 shows the results of replating of primary HPP-CFC colonies as described in the Examples. Primary HPP-CFC colonies were plucked on day 28. Cells from individual primary colonies were replated in methylcellulose under the same conditions used in the primary colony assay. Secondary CFU-GM-derived (hatched bars) and HPP-CFC (solid bars) colonies were enumerated 14 and 28 days later, respectively.

PHPC expansion was investigated by replating day 28 primary HPP-CFC cloned from $R^+$ cells in the presence of c-kit ligand and FP (see FIG. 6). Based on the type of secondary colonies formed after replating, three groups of primary HPP-CFC colonies could be identified. The first group (10%) were unable to sustain the growth of any type of secondary colonies. The second group of colonies (47%) contained cells capable of giving rise to only secondary CFU-GM colonies. Individual primary HPP-CFC colonies of this type each contained between 1 and 25 CFU-GM. Primary HPP-CFC-derived colonies that made up the third group (43% of all colonies analyzed) contained cells that, in addition to being capable of giving rise to secondary CFU-GM colonies (14.2±4.9 [mean±SD]; range 6 to 26 CFU-GM/primary HPP-CFC), also formed secondary HPP-CFCderived colonies. A range of one to six with an average of 3.5 secondary HPP-CFC were formed on the replating of such individual primary HPP-CFC.

EXAMPLE 2

ESTABLISHMENT OF CHIMERAS

CD34+, HLA-DR− Populations.

The cell population used to obtain chimeras of the invention was obtained as follows. Fr 12–14 BM cells were first stained with CD34 (HPCA-1, IgG, isotype) over ice for 20 minutes. Phycoerythrin (PE)-conjugated HLA-DR and isotype-specific, fluorescein isothiocyanate (FITC)-conjugated goat-antimouse IgG$_1$ second step antibody (Southern Biotechnology, Birmingham, Ala.) were then added for another 20 minutes. The cells were then washed and sorted on a Coulter Epics 753 dual-laser flow cytometer (Coulter Electronics, Hialeah, Fla.). See, generally, Srour et al., Cytometry, Vol. 12, p. 179 (1990). Positivity for each fluorochrome was defined as fluorescence greater than 99% of that of controls. This staining protocol allows for the separation of CD34+ HLA-DR−, CD34+ HLA-DR+, CD34− HLA-DR+, and CD34− HLA-DR− cells from within the Fr 12–14 BM cells. In these experiments, CD34+ HLA-DR− cells were collected separately (CD34+ HLA-DR− cells) while the remaining three phenotypes were collected together to constitute what will be referred to herein as complementary cells. Cell viability after sorting was greater than 98%. Separation of CD45+ and CD45− chimetic BM cells was achieved by labeling low density chimeric BM cells obtained by separation over Ficoll/Hypaque with FITC-conjugated CD45 and then isolating CD45+ and CD45− cells by cell sorting as described above. Phenotypic analysis of chimeric and control low-density sheep BM and PB cells and cultured T cells (see discussion of chimeras below) was performed on a FACScan (Becton Dickinson Immunocytometry Systems, San Jose, Calif.) using directly conjugated monoclonal antibodies (MoAbs). All MoAbs were obtained from Becton Dickinson Immunocytometry Systems.

In utero transplantation.

BM graft cells (CD34+, HLA-DR− cells obtained as described above) were injected into several 42- to 48-day old sheep fetuses intraperitoneally through a 22-gauge needle using general techniques as described by Flake et al., Science, Vol. 233, p. 766 (1986). Briefly, the uterus of a pregnant ewe was accessed through a midline laparotomy incision. A traverse incision was then made through the myometrium and chordin. The BM graft was injected intraperitoneally into the fetus after manipulating it into an amniotic bubble. The myometrium was then closed in a double layer and the pregnancy allowed to proceed to term except in two fetuses that were killed in utero 30 days later.

Hematopoietic progenitor cell assays. Cells assayed for the generation of hematopoietic colonies were obtained from the BM of a control sheep, the human donor of the graft, and the chimeric sheep (sheep 4038) as well as CD45+ and CD45− BM cells from sheep 4038 isolated by flow cytometric sorting. Also, a mixture of 95% control sheep and 5% normal human BM cells was prepared and assayed for hematopoietic progenitor cells. Progenitor cell assays were performed as described by Brandt et al., J. Clin. Invest., Vol. 86. p. 932 (1990). Briefly, cells at various concentrations were suspended in 35-mm plastic tissue culture dishes containing 1 mL of 30% fetal bovine serum (FBS), $5\times10^{-5}$ mol/L 2-mercaptoethanol, 1.1% methylcellulose in Iscove's Modified Dulbecco's Medium, and either 1 U human purified erythropoietin (Epo; 50 U/mg protein); Toyobo Co. Ltd., Osaka, Japan) or 1 ng interleukin-3 (IL-3) plus 1 ng granulocytemacrophate colony-stimulating factor (GM-CSF). IL-3 and GM-CFS were obtained from Genzyme Corp (Boston, Me.). The cultures were incubated at 37° C. in a 100% humidified atmosphere of 5% $CO_2$ in air. Erythropoietic colonies (CFU-E) were enumerated after 6 days, whereas erthropoietic bursts (BFU-E) were counted after 9 and 14 days using standard criteria for their identification. See, Brandt et al., Characterization of a Human Hematopoietic Progenitor Cell Capable of Forming Blast Cell Containing Colonies In Vitro, J. Clin. Invest., Vol. 82, p. 1017 (1988). The reported data reflect the number of colonies per $5\times10^4$ plated cells and represent the mean±SE of assays performed in duplicate.

Karyotypic analysis.

To analyze peripheral blood (PB), BM, or cultured cells cytogenetically, the available number of cells was treated in two different ways. Fresh cells were first cultured in 10 mL RPMI 1640+20% FBS, stimulated with 0.12 μg phytohemaglutinin (PHA-HA15); Wellcome Diagnostics, Research Triangle Park, N.C.), and maintained for 72 hours in 5% $CO_2$ at 37° C., then treated with colcemid as described below. Cells obtained from hematopoietic colonies or from cultured T cells were directly treated after harvesting with colcemid. Colcemid was added at 0.18 μg/mL for 35 minutes. The cells were then treated with 0.075 mol/L KCl hypotonic solution for 15 minutes and fixed in 3:1 methanol:acetic acid. Cells were dropped onto cold wet slides and GTG banded.

Propagation of T lymphocytes in vitro.

Propagation of T lymphocytes from sorted chimeric CD45+ and CD45− BM cells was performed as previously generally described. See, Srour et al., Clin. Exp. Immunol., Vol. 80, p. 114 (1990). Briefly, round-bottomed 96-well plates were seeded with $10^4$ irradiated (5,000 rad) cells of the Epstein Barr virus (EBV)-transformed B-cell line JY suspended in RPMI 1640 containing 10% FBS, $5\times10^5$ mol/L 2-mercaptoethanol, 1% final concentration PHA-HA15 (Wellcome Diagnostics), and 5% vol/vol final concentration of T-cell growth factor (TCGF; Cellular Products, Buffalo, N.Y.). Responder cells (CD45+ or CD45− chimeric BM cells) were added at 50 cells per well. The plates were incubated at 37° C. in a 100% humidified atmosphere of 5% $CO_2$ in air for 14 days and were fed with 10 μL/well of TCGF on day 7. Wells seeded with either CD45+ or CD45− BM cells that contained colonies were harvested, pooled, and the cells stained for flow cytometric immunofluorescence analysis as described above.

Variable number tandem repeat polymorphism analysis.

DNA was isolated from BM cells from the chimeric sheep at 3 months after birth, BM cells of a control sheep, and the donor of the human BM graft according to published methods. See, Maniatis et al., Molecular Cloning: A Laboratory Manual, Cold Springs Harbor, N.Y., Cold Spring Harbor Laboratory (1989). DNA was digested by Hat III and electrophoresed on a 1% agarose gel. The gel was then dried and probed directly (see, Cockerill, Anal Biochem., Vol., 168, p. 451 (1988)) with radiolabeled pYNH24 (courtesy of Dr. Y. Nakamura, University of Utah) and MS31 (Cellmark Diagnostics, Germantown, Md.) using a random primed DNA labeling kit (Bothringer Mannheim, Indianapolis, Ind.).

(A) Chimeric sheep 4033, 4035 and 4038.

A total of seven sheep fetuses with gestational ages of between 42 and 48 days were transplanted in utero with fractions of adult human BM cells. See, Flake et al., Science, Vol. 233, p. 766 (1986). Table 14 summarizes the outcome of these transplants. Two animals (4035 and 4026) received $2 \times 10^4$ CD34$^+$ HLA-DR$^-$ cells and $10^6$ irradiated (5,200 rad) complementary cells. The complementary cells were injected with the CD34$^+$ HLA-DR$^-$ cells to act as "carrier" cells that would facilitate the homing of unaltered CD34$^+$ HLA-DR$^-$ cells to the liver or BM. The remaining five animals received unaltered cells from one fraction of cells only or a combination of cells from both fractions. The first test of whether engraftment had been accomplished was conducted approximately 30 days posttransplantation in two animals killed in utero. By karyotypic analysis of more than 200 BM cells, it was determined that 3.8% of total BM cells in sheep 4035 at 1 month after receiving the graft were of human origin. Similarly, fetus 4033, which was transplanted with $2 \times 10^4$ CD34$^+$ HLA-DR$^-$ cells without complementary cells, was found to be a chimera 1 month posttransplantation with 1.5% of the BM cells being of human origin. It was thus calculated that a single femur from sheep 4035 contained $6.5 \times 10^5$ human cells, while that of sheep 4033 contained $3.6 \times 10^5$ human cells. These numbers of human cells detected in a single femur from each fetus represent 32- and 18- fold increases over the number of viable human BM cells originally transplanted into fetuses 4035 and 4033, respectively. The estimates of 32- and 18-fold expansion human cells are at best an underestimate, since only the number of cells in a single femur has been quantitated. BM cells from these fetuses were also assayed for their potential to give rise to human hematopoietic colonies. When cytogenetic analysis of cells from 14-day-old CFU-GM-derived colonies was performed, only human karyotypes were detected, indicating the presence of human myeloid progenitor cells in the BM of the two fetuses.

TABLE 14

Summary of the Outcome of Transplanting Seven Sheep Fetuses With Fractioned Adult Human BM Cells

| Sheep Fetus I.D. No. | Gestational Age When Transplanted (d) | No. and Phenotype of Graft Cells | | Outcome | Engraftment |
|---|---|---|---|---|---|
| | | CD34$^+$ HLA-DR$^-$ | Complimentary Cells | | |
| 4033 | 42 | $2 \times 10^4$ | — | Killed** day 72 | + |
| 4034 | 44 | $2 \times 10^4$ | — | Born Alive | − |
| 4035 | 45 | $2 \times 10^4$ | $1 \times 10^{6*}$ | Killed** Day 72 | + |
| 4036 | 48 | $2 \times 10^4$ | $1 \times 10^{6*}$ | Born Alive | − |
| 4037 | 46 | $4 \times 10^4$ | | Died in Utero | |
| 4038 | 46 | $2 \times 10^4$ | $1 \times 10^6$ | Born Alive*** | + |
| 4039 | 43 | — | $10 \times 10^6$ | Died in Utero | |

*Cells were irradiated (5,200 rad) before injection
**These two animals were killed 1 month after receiving the human BM graft. Karyotypic analysis of BM cells extracted from the femur showed the presence of 1.5% and 3.8% human cells in the BM of fetus 4033 and 4035, respectively.
***Sheep 4038 is the animal studied in detail in the rest of the report.

While two additional animals died in utero, a total of three lambs were born and were therefore available for further examination. Karyotypic analysis of peripheral blood (PB) and bone marrow (BM) samples from two of the three lambs born at term (4034 and 4036 in Table 14) did not show any evidence of engraftment. The third lamb (4038), born alive at term, was found to have engrafted with human BM cells. A detailed analysis of PB and BM samples from sheep 4038 was then conducted at 2 and 3 months postparturition (5 and 6 months posttransplantation).

Fetus 4038 was transplanted at 46 days gestational age with a combination of $2 \times 10^4$ CD34$^+$ HLA-DR$^-$ and $1 \times 10^6$ complementary (see Table 14) human adult BM cells. At 2 months after birth (5 months after engraftment), PB and BM samples from sheep 4038 were obtained for analysis. Low-density BM cells from a control sheep were not reactive with any of the mouse antihuman cell surface marker MoAbs used. However, when BM cells from sheep 4038 were analyzed, it became evident that a fraction of its cells representing 6% of the low-density BM cells analyzed was reactive with the leukocyte common antigen CD45 that identifies a family of glycoproteins (180 to 220 that are expressed on the surface of a variety of human hematopoietic cells. See, Ralph et al., EMBO, Vol., 6, p. 1251 (1987). To further examine the nature of these human cells, lineage-specific MoAbs were used. Human T lymphocites expressing either CD8 (1.1%) or CD4 (0.9%) were detected in the chimeric BM. Similarly, B lymphocytes (2% CD19$^+$ cells) and cells reactive with CD16 and CD56, and therefore presumably human natural killer (NK) cells, (see, Lanier et al., J. Immunol. Vol. 136, p. 4480 (1986)) were also identified. Cells expressing HLA-DR were detected. CD34$^+$ cells were not convincingly detected flow cytometrically in this animal; however, this is not surprising because CD34$^+$ cells normally represent on the average 1% or less of total human BM cells, (see, Civin et al., Antigenic Analysis of Hematopoiesis VI Flow Cytometric Characterization of MY-10-Positive Progenitor Cells in Normal Bone Marrow, Exp. Hematol., Vol. 15, p. 10 (1987) and such a small percentage of cells (0.06% when considering that only 6% of the chimeric BM cells are human) would be difficult to detect.

Cells expressing human cell surface markers were also apparent among the PB cells of sheep 4038. The various cell lineages, however, were present in the PB at lower percentages than what was observed in BM. Of particular interest is the fact that PB CD4$^+$ or CD8$^+$ T lymphocytes were present in numbers threefold to fivefold less than those found in BM, even though a total of 2.5% of PB cells expressed CD3. Chimeric PB also contained human NK cells, as evidenced by the detection of cells expressing CD16 and CD56, as well as a small percentage (0.2%) of CD19 lymphocytes. PB cells from a control sheep were completely unreactive with the MoAbs used in these assays.

Although the use of this battery of mouse MoAbs recognizing human cell surface antigens proved to be species specific, two alternative methods to document the presence of human cells in the PB and BM of sheep 4038 were used to confirm the sustained engraftment. First, cytogenetic analysis was implemented to examine the karyotypes of cells present in the PB of sheep 4038 at 5 months after engraftment. Among 87 total cells examined from a preparation, 12 cells had a human karyotype. In another assay, the pattern obtained in a variable number tandem repeat analysis of donor-derived BM DNA was compared with that obtained from DNA isolated from BM cells from sheep 4038 six months after engraftment. The variable number tandem repeat pattern of DNA isolated from the BM of sheep 4038 was completely homologous to that of donor derived DNA. These data demonstrated the persistence of chimerism in this sheep at 6 months posttransplantation.

Using the different electrophoretic mobilities of human and sheep hemoglobins in a variety of gel matrices, the presence of human hemoglobin in the peripheral blood of the chimeric sheep 4038 was not detected. Another examination was made to determine whether the human cells detected in the BM of sheep 4038 contained human hematopoietic proginitor cells capable of generating hematopoietic colonies in vitro. These studies took advantage of the kinetics of appearance in vitro of sheep and human hematopoietic colonies. In the presence of recombinant human Epo, CFU-E- and BFU-E-derived colonies present in the BM of a control sheep appeared on days 6 and 9 of culture, respectively. These colonies, however, degenerated by day 14. Similarly, when cultured in the presence of human recombinant IL-3 and GM-CSF, few sheep CFU-GM-derived colonies appeared by day 9. When chimeric BM cells (obtained at 5 months after engraftment) were cultured under the same conditions, about 10-fold and sixfold more BFU-E and CFU-GM-derived colonies, respectively, were present on day 14 as compared with the number of colonies present on day 14 in cultures of control sheep BM cells. The presence of BFU-E-derived colonies with human BFU-E growth kinetic characteristics suggests that human erythropoiesis was established in this animal, albeit not to a sufficient level to allow detection of human hemoglobin in the PB of this animal. On day 14, cells from CFU-GM-derived colonies in cultures initiated with chimeric BM cells were plucked, washed, and prepared for karyotypic analysis. Although the karyotype of only a few cells could be positively identified, all of these cells were of human origin.

To further confirm that human progenitor cells were present in the chimeric BM of sheep 4038, flow cytometric cell sorting was used. From $2.5 \times 10^6$ chimeric BM cells stained with CD45, two fractions of cells enriched for cells expressing CD45 ($4.8 \times 10^4$ cells recovered) and a second fraction consisting of CD45$^-$ ($<3 \times 10^5$ cells recovered) BM cells. Both sorted fractions of CD45$^+$ and CD45$^-$ BM cells were cultured in semi-solid medium in the presence of human recombinant IL-3 and GM-CSF. See, Brandt, et al., *J. Clin. Invest.*, Vol. 86, p. 932 (1990). CD45$^+$ cells gave rise to 40 granulocyte-macrophage colonies after 14 days in culture, whereas CD45$^-$ cells gave rise to only three such colonies. Once again, karyotypic analysis of cells plucked from CFU-GM colonies assayed from CD45$^+$ cells only showed cells with human chromosomes.

Another determinant of the success of BM transplantation is the capacity of the graft to establish and maintain a functional lymphoid system within the host. Flow cytometric analysis of MB and PB cells from sheep 4038 at 5 months posttransplantation indicated the presence of cells expressing CD19. To examine whether the human BM graft produced functional T lymphocytes in the chimeric animal, BM cells from sheep 4038 at 2 months after birth were tested for their mitogenic response in vitro. Sorted CD45$^+$ and CD45$^-$ chimeric BM cells were cultured for 14 days in the presence of IL-2 and phytohemagglutinin (PHA) over a feeded layer of irradiated DBV-transformed B cells. See, Srour et al., *Clin. Exp. Immunol.*, Vol. 80, p. 114 (1990). Cells from the developing T-lymphocyte colonies were collected 14 days later and their phenotype was determined flow cytometrically. The results of the analysis of cells collected from T-lymphocyte colonies generated from CD54$^+$ and CD45$^-$ fractions of chimeric BM showed that colonies that developed from CD45$^-$ T cells contained cells that failed to react with any of the human T-cell-specific MoAbs as well as with CD45 and HLA-DR. On the other hand, CD45$^+$ BM cells gave rise to colonies containing cells greater than 98% of which were CD45$^+$ and CD3$^+$. In addition 89.4% of these cells were positive for the expression of CD7, while 57.0% were CD8$^+$ and 30.8% CD4$^+$. As expected most of the cells being activated with PHA and IL-2 expressed HLA-DR. Karyotypic analysis of T lymphocytes collected from colonies generated by CD45$^+$ chimeric BM cells once again showed a full complement of human chromosomes while no sheep karyotypes were detected.

(B) Chimeric sheep 273, 298 and 306.

Using techniques as described above, several fetal sheep were transplanted in utero at 45 to 50 days gestational age with isolated human CD34$^+$ HLA-DR$^-$ BM cells only (obtained as above, and in the absence of complementary cells). Three animals born alive were documented at 120 days post-transplantation to express human cells constituting 8.5% (sheep 273), <1% (sheep 298) and 11% (sheep 306) of chimeric BM cells. Chimerism in these animals was documented by the detection of cells expressing the human common leukocyte antigen CD45 which does not react with sheep cells. Although the BM of sheep 298 contained detectable CD45$^+$ cells, PB from this animal failed to express any of these lineage markers. However, karyotypic analysis of PB samples from these animals detected cells with human karyotypes only in sheep 273 and 306. In addition, PB from these two animals (273 and 306) contained CD45, CD14, CD4, CD8, CD19, and CD16/CD56 positive human cells. In vitro colony assays indicated that BM from all three animals contained human hematopoietic progenitor cells. Chimerism in animals 273 and 306 was documented by the detection of CD45$^+$ cells and was reconfirmed again 140 days post-engraftment. At this time point no human cells could be detected in the BM of sheep 298. Animals 273 and 306 continued to express human cells up to day 220 post-transplantation. During this time, assays aimed at examining the different lineages expressed in these chimeric animals were conducted.

Detection of myeloid, erythroid, and megakaryocytic lineages in chimeric sheep.

The ability of chimeric BM cells to form human hematopoietic colonies was assessed 190 days following in utero transplantation. Human cells present within the chimeric BM of sheep 273 and 306 were identified and isolated by flow cytometric cell sorting based on their reactivity with CD45. Isolated CD45$^+$ (human in origin) and CD45$^-$ (sheep in origin) cells were used along with human and control sheep BM cells in hematopoietic progenitor cell assays to determine which human cell lineages were being expressed in the transplanted sheep. The assays were evaluated on day 12 for the enumeration of colony forming unit-megakaryocyte (CFU-MK), on day 14 for the enumeration of BFU-E. CFU-GM, and CFU-GEMM and on day 28 for the presence of HPP-CFC. Whereas control sheep BM cells and CD45$^-$ cells from sheep 273 and 306 failed to give rise to any CFU-MK-derived colonies, CD45$^+$ cells from both animals contained megakaryocytic progenitor cells. Similar results were obtained for both BFU-E-and CFU-GEMM-derived colonies. However, CD45$^+$ cells from sheep 306 did not give rise to these types of colonies although in a previous similar experiment conducted 144 days post-transplantation, BM cells from sheep 306 generated BFU-E-and CFU-GEMM-derived colonies. Also, at 190 days post-transplantation, CD45$^+$ cells from sheep 273 and 306 contained granulocytic/monocytic progenitor cells in numbers equal to or in excess of those detected in normal human low density BM cells. The fact that some CFU-GM-derived colonies were observed in marrow cells of a control sheep and in the CD45$^-$ fraction of sheep 273 and 306 BM cells is not surprising. Although sheep marrow cells do not respond maximally to stimulation with human recombinant cytokines, a partial response is usually detected.

Nevertheless, the number of CFU-GM observed in the control sheep BM cells and in sheep 273 and 306 CD45⁻ cells was substantially less than that observed in plates seeded with human BM cells or with the CD45⁺ cells from these two animals. It is interesting that chimeric BM cells from sheep 273 contained one of the most primitive hematopoietic progenitor cells, the HPP-CFC. In these experiments HPP-CFC were present in the CD45⁺ fraction of sheep 273 BM and in normal human BM cells only indicating that the colonies detected in the chimeric BM must be of human origin.

Establishment of lymphopoiesis in transplanted animals.

Having demonstrated the presence of myeloid, erythroid and megakaryocytic progenitor cells in the BM of sheep 273 and 306, it was of interest to investigate whether these marrows also contained functional human lymphoid elements. To that effect, chimeric BM cells obtained from both sheep 190 days post-transplantation were first separated by flow cytometric cell sorting in to CD45⁺ and CD45⁻ fractions. Sorted cells were then used in a T cell proliferation assay to detect functional T lymphocytes and in an in vitro Ig production assay to assess if human B cells present in the chimeric animals were functional and capable of producing Ig. By these analyses it was demonstrated that human T cells expressing CD3, CD4, and CD8, as well as NK cells (cells positive for CD16 and CD56) were generated in vitro from CD45⁺ cells in response to phytohemaglutinin and IL-2. Cells generated in these assays from CD45⁻ cells failed to react with any of the cell lineage specific monoclonal antibodies used in these experiments. The results obtained from the in vitro Ig production assays performed with CD45⁺ and CD45⁻ chimeric BM cells as well as control sheep and human BM cells demonstrated that whereas human BM cells produced both IgG and IgM immunoglobulins, control sheep BM cells as well as CD45⁻ cells from sheep 273 and 306 failed to produce any detectable human Ig. In contrast, CD45⁺ cells from both transplanted animals produced detectable amounts of human IgG. The fact that IgG was produced from chimeric cells indicates that these human B cells are indeed functional and capable of undergoing Ig switch.

Evidence of self-renewal in transplanted sheep.

With self-renewal being a seminal functional parameter of HSC, whether the human BM graft used in these experiments contained cells capable of self-regeneration was investigated. To achieve this, chimeric BM cells collected 120 days post-transplantation were analyzed flow cytometrically for the presence of CD34⁺ HLA-DR⁻ cells. Since human cells in the chimeric BM constituted a small fraction of total BM cells, human CD45⁺ cells were first isolated by flow cytometric cell sorting and then stained and analyzed for the expression of CD34 and HLA-DR. The phenotype of cells used initially as a BM graft was detected in sheep BM. In addition, cells expressing other human lineages were also detected with such analysis. It is of interest to note that the percentage of chimeric human BM cells expressing the CD34⁺ HLA-DR⁻ phenotype was higher than what is normally present in human BM cells. It is possible that a selective pressure to proliferate and expand was exerted on human CD34⁺ by the "non-permissive" sheep BM microenvironment. The fact that a higher percentage of human CD34⁺ cells existed in the chimeric BM than in normal BM may in turn explain why a higher number of human hematopoietic colonies was detected in the former than in the latter.

Taken together, these data demonstrate that the BM grafts transplanted into fetal sheep in these studies consist of human HSC capable of both pluripotent differentiation and self-renewal. It is also apparent from these studies that the sheep-human model of xenogeneic stem cell transplantation provides a unique avenue for the in vivo examination of human hematopoiesis. Although several other animal models have been previously utilized for this purpose, none has had much success without the co-transplantation into the host animals of other human tissues in addition to hematopoietic cells nor was any capable of supporting pluripotential lymphohematopoiesis as demonstrated by applicants' work. In fact, differentiation of human cells in some of these animal models has been reported to occur in the transplanted human tissues, such as human thymus, and not in the animal host per se suggesting that these models represent no more than just a modified form of allogeneic BM transplantation rather than a xenogeneic model of human hematopoiesis. In addition, most of the animal models utilizing immunodeficient mice sustain human hematopoiesis for shorter periods of time than what is achieved in this model. Zanjani et al. have reported substantially longer periods of engraftment following transplantation of fetal sheep with human fetal liver cells.

Thus the applicants have demonstrated for the first time the ability of a given phenotype of human BM cells to undergo multipotential lymphohematopoiesis and self-renewal in a single "assay system". In fact these data are the first ever to show that a well characterized, phenotypically homogeneous population of BM cells was capable of multipotential differentiation simultaneously giving rise to cells belonging to the erythrocytic, megakaryocytic, granulocytic as well as the B, T, and NK lymphoid lineages. Also important is the fact that it is an in vivo model of human hematopoiesis and that it allows for the in vivo self-renewal of HSC. Since in these studies on CD34⁺ HLA-DR⁻ BM cells constituted the stem cell grafts it becomes clear that not only are these cells responsible for the observed engraftment but that this phenotype of BM cells is identified with the human pluripotential hematopoietic stem cell. In addition to other utilities, the successful engraftment of fetal sheep with purified adult human HSC evidence the applicability of such cells and cells from other like sources (e.g. fetal liver, umbilical cord blood, peripheral blood) to prenatal stem cell transplantation in humans for the correction of several hematological and metabolic disorders. The data from the applicants' discoveries suggest that such purified HSC could be used across histocompatibility barriers providing ample supply of stem cells for transplantation patients.

While the invention has been illustrated and described in the foregoing description, the same is to be considered as illustrative and not restrictive in character, it being understood that only the preferred embodiments have been shown and described and that all changes and modifications that come within the spirit of the invention are desired to be protected.

All publications cited herein are hereby incorporated by reference herein as if each were individually incorporated and fully set forth. Additional information may be found in U.S. Pat. No. 5,061,620 and in Srour et al, Blood, Vol. 79, No. 6, pp. 1404–1412 (1992); Srour et al., Blood, Vol. 81, pp. 661–669 (1993); and Briddell et al., Blood, Vol. 79, pp. 3159–3167 (1992), which are also hereby incorporated by reference herein in their entirety.

What is claimed is:

1. A method of obtaining persistent maintenance of grafted human hematopoietic cells in a mammal, comprising the step of grafting the mammal in utero with a pluripotent human stem cell (PHSC) containing population of non-fetal human hematopoietic cells characterized as $CD34^+$ and which undergo self-renewal and differentiation to members of the lymphoid, myeloid, erythroid and megakaryocytic lineages when cultured in vitro.

2. A method according to claim 1, wherein said population of non-fetal human hematopoietic cells are further characterized as $HLA-DR^-$.

3. A method according to claim 1, wherein said human hematopoietic stem cells are derived from adult human bone marrow.

4. A method according to claim 1, wherein said human hematopoietic stem cells are derived from human umbilical cord blood.

5. A method according to claim 1, wherein said human hematopoietic stem cells are derived from human peripheral blood.

* * * * *